(12) United States Patent
Miekka et al.

(10) Patent No.: US 6,946,098 B2
(45) Date of Patent: Sep. 20, 2005

(54) METHODS FOR STERILIZING BIOLOGICAL MATERIALS

(75) Inventors: Shirley I. Miekka, Gaithersburg, MD (US); Wilson Burgess, Clifton, VA (US); William N. Drohan, Springfield, VA (US); Yuri Griko, Gaithersburg, MD (US); Martin J. MacPhee, Montgomery Village, MD (US); David M. Mann, Gaithersburg, MD (US)

(73) Assignee: Clearant, Inc., Los Angeles, CA (US)

( * ) Notice: Subject to any disclaimer, the term of this patent is extended or adjusted under 35 U.S.C. 154(b) by 272 days.

(21) Appl. No.: 09/925,620

(22) Filed: Aug. 10, 2001

(65) Prior Publication Data

US 2003/0031581 A1 Feb. 13, 2003

(51) Int. Cl.$^7$ .............................. A61L 2/08; A01N 1/02
(52) U.S. Cl. ............................................. 422/22; 435/2
(58) Field of Search .......................... 422/22, 28; 435/2

(56) References Cited

U.S. PATENT DOCUMENTS

| | | |
|---|---|---|
| RE23,195 E | 2/1950 | Brasch |
| 2,832,689 A | 4/1958 | Proctor et al. |
| 2,920,969 A | 1/1960 | Stoddard |
| 2,962,380 A | 11/1960 | Wertheim |
| 3,620,944 A | 11/1971 | Tanito |
| 3,743,480 A | 7/1973 | Falk |
| 3,779,706 A | 12/1973 | Nablo |
| 3,962,038 A | 6/1976 | Kawashima et al. .......... 195/68 |
| 4,136,094 A | 1/1979 | Condie |
| 4,251,437 A | 2/1981 | Rasmussen et al. |
| 4,282,863 A | 8/1981 | Beigler et al. |
| 4,330,626 A | 5/1982 | Blair et al. |
| 4,336,247 A | 6/1982 | Eriksen |
| 4,370,264 A | 1/1983 | Kotitschke et al. |
| 4,409,105 A | 10/1983 | Hayashi et al. |
| 4,472,840 A | 9/1984 | Jefferies |
| 4,620,908 A | 11/1986 | Van Duzer |
| 4,727,027 A * | 2/1988 | Wiesehahn et al. ...... 435/173.2 |
| 4,784,850 A | 11/1988 | Abraham |
| 4,798,611 A | 1/1989 | Freeman, Jr. |
| 4,865,602 A | 9/1989 | Smestad et al. |
| 4,877,866 A | 10/1989 | Rudnick et al. ............ 530/387 |
| 4,894,253 A | 1/1990 | Heineman et al. ............ 427/36 |
| 4,931,361 A | 6/1990 | Baldeschwieler et al. |
| 4,933,145 A | 6/1990 | Uchida et al. |
| 4,946,648 A | 8/1990 | Dichtelmüller et al. |
| 4,963,356 A | 10/1990 | Calenoff et al. |
| 4,994,237 A | 2/1991 | Login et al. .................. 422/21 |
| 5,000,951 A | 3/1991 | Bass et al. |
| 5,002,766 A | 3/1991 | Ransberger et al. ....... 424/94.2 |
| 5,012,503 A | 4/1991 | Nambu et al. |
| 5,044,091 A | 9/1991 | Ueda et al. |
| 5,106,619 A | 4/1992 | Wiesehahn et al. |
| 5,134,295 A | 7/1992 | Wälischmiller |
| 5,185,371 A | 2/1993 | Rubinstein |
| 5,226,065 A | 7/1993 | Held et al. |
| 5,283,034 A | 2/1994 | Okrongly et al. |
| 5,362,442 A | 11/1994 | Kent |
| 5,418,130 A | 5/1995 | Plat et al. |

(Continued)

FOREIGN PATENT DOCUMENTS

| | | |
|---|---|---|
| CA | 2056619 | 10/1991 |
| EP | 310 316 | 4/1989 |
| EP | 334 679 | 9/1989 |
| EP | 919 918 A2 | 6/1999 |
| EP | 919 918 A3 | 6/1999 |
| EP | 0808167 B1 | 6/2002 |
| EP | 0820301 B1 | 7/2002 |
| JP | 408098688 A | 4/1996 |
| JP | 11-216147 | 8/1999 |
| SU | 1321420 A | 7/1987 |
| WO | WO 90/00907 | 2/1990 |
| WO | WO 91/16060 | 10/1991 |
| WO | WO 95/03071 | 2/1995 |
| WO | WO 00/25839 | 3/2000 |
| WO | WO 00/28552 | 5/2000 |
| WO | WO 00/52031 | 9/2000 |
| WO | WO 01/08611 A1 | 2/2001 |
| WO | WO 01/12318 A1 | 2/2001 |
| WO | WO 01/32107 A2 | 5/2001 |
| WO | WO 01/32110 A2 | 5/2001 |
| WO | WO 01/45720 A1 | 6/2001 |
| WO | WO 01/49219 A1 | 7/2001 |
| WO | WO 01/72233 A1 | 10/2001 |
| WO | WO 01/72244 A1 | 10/2001 |
| WO | WO 01/91818 A1 | 12/2001 |

OTHER PUBLICATIONS

Salim–Hanna, M. et al. Abstract of "Free radical scavenging activity of carnosine," Free Radical Research Communications (1991), 14(4), pp. 263–270.*

Robert J. Woods, "Food Irradiation," Endeavor, New Series, vol. 18, No. 3, 1994, pp. 104–108.

A. Dziedzic–Goclawska et al., "Sterilisation of Tissue Allografts," Advances in Tissue Banking, vol. 1, pp. 261–321, prior art.

M.J. Goertzen et al., "Sterilisation of Canine Anterior Cruciate Allografts by Gamma Irradiation in Argon," Journal of Bone and Joint Surgery (Corrections), vol. 77–B, No. 2, Mar. 1995, pp. 205–212.

Potier, M. et al., Radiation Inactivation of Proteins: Temperature–Dependent Inter–Protomeric Energy Transfer in Ox Liver Catalase, Biochem. J., 298:571–574 (1994).

(Continued)

Primary Examiner—Elizabeth McKane
(74) Attorney, Agent, or Firm—Morgan, Lewis & Bockius LLP

(57) ABSTRACT

Methods are disclosed for sterilizing biological materials to reduce the level therein of one or more biological contaminants or pathogens, such as prions, responsible for the disease states known as transmissible spongiform encephalopathies (TSEs) in mammals. These methods involve sterilizing biological materials with irradiation.

70 Claims, 9 Drawing Sheets

U.S. PATENT DOCUMENTS

| | | | | |
|---|---|---|---|---|
| 5,460,962 | A | 10/1995 | Kemp | |
| 5,510,122 | A | 4/1996 | Sreebny et al. | |
| 5,548,066 | A | 8/1996 | Leneau et al. | |
| 5,603,894 | A | 2/1997 | Aikus et al. | |
| 5,609,864 | A | 3/1997 | Shanbrom | |
| 5,637,451 | A | 6/1997 | Ben-Hur et al. | |
| 5,643,464 | A | 7/1997 | Rhee et al. | |
| 5,712,086 | A | 1/1998 | Horowitz et al. | |
| 5,730,933 | A | 3/1998 | Peterson | |
| 5,817,528 | A | 10/1998 | Böhm et al. | |
| 5,837,313 | A | 11/1998 | Ding et al. | |
| 5,856,172 | A | 1/1999 | Greenwood et al. | |
| 5,881,534 | A | 3/1999 | Ahlqvist et al. | |
| 5,911,951 | A | 6/1999 | Girardot et al. | 422/28 |
| 5,912,241 | A * | 6/1999 | Gottlieb et al. | 514/185 |
| 5,958,669 | A | 9/1999 | Ogle et al. | 435/1.1 |
| 5,965,349 | A | 10/1999 | Lin et al. | 435/2 |
| 5,981,163 | A | 11/1999 | Horowitz et al. | |
| 5,986,168 | A | 11/1999 | Noishiki | |
| 5,989,498 | A | 11/1999 | Odland | |
| 6,010,719 | A | 1/2000 | Remon et al. | |
| 6,046,024 | A | 4/2000 | Burton et al. | |
| 6,049,025 | A | 4/2000 | Stone et al. | |
| 6,060,233 | A | 5/2000 | Wiggins | |
| 6,066,626 | A | 5/2000 | Yew et al. | |
| 6,087,141 | A | 7/2000 | Margolis-Nunno et al. | |
| 6,120,592 | A | 9/2000 | Brault et al. | |
| 6,159,490 | A | 12/2000 | Deghenghi | |
| 6,171,549 | B1 | 1/2001 | Kent | |
| 6,187,572 | B1 | 2/2001 | Platz et al. | |
| 6,190,855 | B1 | 2/2001 | Herman et al. | |
| 6,197,207 | B1 | 3/2001 | Chapman et al. | |
| 6,203,544 | B1 | 3/2001 | Gotzen | |
| 6,214,534 | B1 | 4/2001 | Horowitz et al. | |
| 6,235,508 | B1 | 5/2001 | Sowemimo-Coker et al. | |
| 6,258,821 | B1 | 7/2001 | Stogniew et al. | |
| 6,312,931 | B1 | 11/2001 | O'Dwyer et al. | 435/173.1 |
| 6,346,216 | B1 | 2/2002 | Kent | 422/22 |
| 6,358,284 | B1 | 3/2002 | Fearnot et al. | 623/23.72 |
| 6,375,989 | B1 | 4/2002 | Badylak et al. | 424/551 |
| 6,383,732 | B1 | 5/2002 | Stone | 435/1.1 |
| 6,383,810 | B2 | 5/2002 | Fike et al. | 435/384 |
| 6,384,419 | B1 | 5/2002 | Purtle | 250/526 |
| 6,461,630 | B1 | 10/2002 | Tucker et al. | 424/423 |
| 6,485,723 | B1 | 11/2002 | Badylak et al. | 424/93.7 |
| 2001/0049141 | A1 | 12/2001 | Fike et al. | 435/384 |
| 2002/0064807 | A1 | 5/2002 | Badylak et al. | 435/34 |
| 2002/0106394 | A1 | 8/2002 | Tucker et al. | 424/423 |
| 2002/0188319 | A1 | 12/2002 | Morris et al. | 606/213 |
| 2003/0068815 | A1 | 4/2003 | Stone et al. | 435/325 |

OTHER PUBLICATIONS

Sakai, T. et al., Microbiological Studies on Drugs and Their Raw Materials. IV. Sterilization of Microbial Contaminants in Enzyme Powder by Gamma Irradiation, Chem. Pharm. Bull., 26:1130–1134 (1978).

Salim-Hanna. M. et al., Free Radical Scavenging Activity Of Carnosine, Free Rad. Res. Comms., 14:263–270 (1991) (Harwood Academic Publishers GmbH).

Song, K.B. et al., Effect of Gamma–irradiation on the Physicochemical Properties of Blood Plasma Proteins, 2002 Annual Meeting and Food Expo–Anaheim, California, Session 30C–1, Food and Chemistry: Proteins (Jun. 2002) (Abstract).

Suomela, H., Inactivation of Viruses in Blood and Plasma Products, Transfusion Medicine Reviews, 7:42–57 (1993) (W.B. Saunders Company).

(Abstract of EP0919198A2 and EP0919198A3 (Delphion–DERABS Abstract #G1999–304614)), prior art.

Website: www.wslfweb.org/docs/dstp2000.stopdf/19–MD.pdf, (Defense Science and Technology Plans, (Feb. 2000) p. 176, Section II, MD.03, U.S. Department of Defense Deputy Under Secretary of Defense (Science and Technology)).

Website: www.usacc.org/attaccc/ppt.html, (Advanced Technology Applications for Combat Casualty Care, 2001 Presentations, U.S. Army Medical Research and Material Command Combat Casualty Care Research Program (2001)).

Website: www.usacc.org/RevisedStepB.html, Bakaltcheva, I. et al., (FY01 Request for Proposals–Intramural–Revised 2, Combat Casualty Care Research Program, (2000)).

Website: www.benvue.com/history/history_content.html, (2002).

Website: www.phase–technologies.com/html/vol.2no1.html, Jennings, T.A., (Glossary of Terms for Lyophilization) (1999).

Website: www.phase–technologies.com/html/vol.1no9.html, Jennings, T.A., (Overview of the Lypholization Process) (1998).

Website: www.phase–technologies.com/html/vol.1no2.html, Jennings, T.A., (Role of Product Temperature in the Lypholization Process, prior art.

Website: www.phase–technologies.com/html/vol.2no2.html, Jennings, T.A., (What I Wish I Knew About Lyophilization) (1999).

Website: www.phase–technologies.com/html/vol.1no7.html, Jennings, T.A., (Which Shelf Temperature During Lyophilization?) (1998).

Website: www.phase–technologies.com/html/vol.1no10.html, Jennings, T.A., (Yes, You have no Eutectic) (1998).

Chanderkar, L.P. et al., Radiation–Induced Changes In Purified Prothrombin and Thrombin, Biochimica et Biophysica Acta, 706:1–8 (1982) (Elsevier Biomedical Press).

Dyskin, E.A. et al., Hemomicrocirculatory Bed in the Wall of Hollow Organs of the Dog Gastrointestinal Tract at Portal Hypertension, Arkh Anat Gistol Embiol, 93:58–68 (1987).

Chin, S. et al., Virucidal Treatment of BLood Protein Products With UVC Radiation, Photochemistry and Photobiology, 65:432–435 (1997) (American Society for Photobiology).

Ghosh, M.M. et al., A Comparison of Methodologies for the Preparation of Human Epidermal–Dermal Composites, Annals of Plastic Surgery; 39:390–404 (1997) (Lippincott–Raven Publishers).

Hsiue, G. et al., Absorbable Sandwich–Like Membrane for Retinal–Sheet Transplantation, pp. 20–25 (2002) (Wiley Periodicals, Inc).

Jensen, J. et al., Membrane–bound Na, K–ATPase: Target Size and Radiation Inactivation Size of Some of Its Enaymatic Reactions, J. Biological Chemistry, 263:18063–18070 (1988) (Am. Soc. for Biochem. and Mol. Biol.).

Kamat, H.N. et al., Correlation of Structural Alterations in Bovine Fibrinogen with Loss of Clotting Properties After Gamma Irradiation, Radiation Research, 49:381–389 (1972) (Academic Press, Inc.).

Kempner, E.S. et al., Effect of Environmental Conditions on Radiation Target Size Analyses, Analytical Biochemistry, 216:451–455 (1994).

Kempner, E.S. et al., Radiation–Damaged Tyrosinase Molecules are Inactive, Biophysical Journal, 55:159–162 (1989) (Biophysical Society).

Kuijpers, A.J. et al., In vivo Compatibility and Degradation of Crosslinked Gelatin Gels Incorporated in Knitted Dacron, pp. 137–144 (2000) (John Wiley & Sons, Inc.).

Le Maire, M. et al., Effects of Ionizing Radiations on Proteins, Journal of Biochem., 267:431–439 (1990).

Ma, J.T. et al., Functional Size Analysis of F–ATPase from *Escherichia coli* by Radiation Inactivation, The Journal of Biological Chemistry, 268:10802–10807 (1993) (The Am. Soc. for Biochem. and Mol. Bio., Inc.).

Marx, G. Protecting Fibrinogen with Rutin During UVC Irradiation for Viral Inactivation, Photochemistry and Photobiology, 63:541–546 (1996) (American Society for Photobiology).

Nagrani, S. et al., The Radiation–Induced Inactivation of External Yeast Invertase in Dilute Aqueous Solution, Int. J. Radiat. Biol., 55:191–200 (1989) (Taylor & Francis Ltd.).

Nielsen, M. et al., The Apparent Target Size of Rat Brain Benzodiazepine Receptor, Acetylcholinesterase, and Pyruvate Kinase Is Highly Influenced by Experimental Conditions, The Journal of Biological Chemistry, 263:11900–11906 (1988) (The American Society for Biochemistry and Molecular Biology, Inc.).

Plavsic, Z. M. et al., Resistance of Porcine Circovirus to Gamma Irradation, BioPharm, pp. 32–36 (Apr. 2001).

Blanchy, B.B. et al., Immobilization of Factor VIII on Collagen Membranes, J. Biomedical Materials Research, 20:469–479 (1986) (John Wiley & Sons, Inc.).

Borisova, E.A. et al., Protein Degradation During Interphase Death of Thymocytes Induced by Radiation and Dexamethasone, pp. 519–521 (1990).

Boyer, T.D. et al., Radiation Inactivation of Microsomal Glutathione S–Transferase, The Journal of Biological Chemistry, 261:16963–16968 (1986).

Chanderkar, L.P. et al., The Involvement of Aromatic Amino Acids in Biological Activity of Bovine Fibrinogen as Assessed bye Gamma–Irradiation, Radiation Research, 65:283–291 (1976) (Academic Press, Inc.).

A. Salehpour et al., Dose–Dependent Response of Gamma Irradiation on Mechanical Properties and Related Biochemical Composition of Goat Bone–Patellar Tendon–Bone Allografts, 1995, pps. 898–906, The Journal of Orthopaedic Research, vol. 13.

Nikolaus Schwarz et al., Irradiation–sterilization of Rat Bone Matrix Gelatin, 1988, pps. 165–167, Acta Orthop Scand, vol. 59, No. 2.

C.W. Smith et al., Mechanical Properties of Tendons: Changes With Sterilization and Preservation, Feb. 1996, pps. 56–61, Journal of Biomechanical Engineering, vol. 118.

Yukiyoshi Toritsuka et al., Effect of Freeze–Drying or γ–Irradiation on Remodeling of Tendon Allograft in a Rat Model, 1997, pps. 294–300, Journal of Orthopaedic Research, vol. 15.

Konrad Wangerin et al., Behavior of Differently Sterilized Allogenic Lyophilized Cartilage Implants in Dogs, 1987, pps. 236–242, J. Oral Maxillofac Surg, vol. 45.

S. Wientroub et al., Influence of Irradiation on the Osteoinductive Potential of Demineralized Bone Matrix, 1988, pps. 255–260, Calcified Tissue International, vol. 42.

Maria Raptopoulou–Gigi et al., Antimicrobial Proteins in Sterilised Human Milk, Jan. 1, 1977, pps. 12–14, British Medical Journal, vol. 1.

Edward A. Rittenhouse et al., Sterilization of Aortic Valve Grafts for Transplantation, Jul. 1970, pps. 1–5, Aortic Valve Grafts for Transplantation, Archives of Surgery, vol. 101, No. 1.

H. Sato et al., Sterilization of Therapeutic Immunoadsorbents by Ionizing Radiation, 1986, pps. 131–136, The International Journal of Artificial Organs, vol. 9, No. 2.

Richard A. Smith et al., Gamma Irradiation of HIV–1, 2001, pps. 815–819, Journal of Orthopaedic Research, vol. 19.

Barbara Lüssi–Schlatter et al., Die Antimikrobielle Behandlung von Peroralen Enzympräparaten mit Gamma–Strahlen, Pharmazeutisches Institut der Eidgenössischen Technischen Hochschule Zürich Galenische Abteilung, prior art.

Martindale's Extra Pharmacopoecia, Glucose p. 1265; prior art.

The Merck Index, Eleventh Edition Glucose pp. 4353–4354, prior art.

G.L. Moore et al., Effects of 4000 Rad. Irradiation on the In Vitro Storage Properties of packed Red Cells, Nov.–Dec. 1985, pps. 583–585, Final Rept., Pub. In Transfusion, vol. 25, No. 6 (Abstract).

Shcheglova et al., The Effect of the Power of Gamma–Radiation on the Radiation Dose in the Sterilization of Drugs, 1984, pps. 730–732, Khim–Farm Zh, vol. 18, No. 6 (Abstract).

G.A. Yarygina, Dose Rate Effect on Survival of Microorganisms Used As Test–Cultures in Radiation Sterilization of Medical Products, 1973, pps. 32–39, Radiats. Tekh., No. 9 (Abstract).

O. Cornu et al., Effect of Freeze–Drying and Gamma Irradiation on the Mechanical Properties of Human Cancellous Bone, 2000, pps. 426–431, Journal of Orthopaedic Research, vol. 18.

Anna Dziedzic–Goclawska et al., Effect of Radiation Sterilization on the Osteoinductive Properties and the Rate of Remodeling of Bone Implants Preserved by Lyophilization and Deep–Freezing, Nov. 1991, pps. 30–37, Clinical Orthopaedics and Related Research, vol. 272.

Ole T. Jensen et al., Vertical Guided Bone–Graft Augmentation in a New Canine Mandibular Model, Nov. 3, 1995, pps. 335–343, The International Journal of Oral and Maxillofacial Implants, vol. 10.

Ronald W. Katz et al., Radiation–Sterilized Insoluble Collagenous Bone Matrix is a Functional Carrier of Osteogenin for Bone Induction, 1990, pps. 183–185, Calcified Tissue International, vol. 47.

Everard Munting et al., Effect of Sterilization on Osteoinduction, 1988, pps. 34–38, Acta Orthop Scand, vol. 59, No. 1.

P.A. Puolakkainen et al., The effect of Sterilization on Transforming Growth Factor β Isolated From Demineralized Human Bone, 1993, pps. 679–685, Transfusion, vol. 33, No. 8.

U. Ripamonti et al., Long–Term Evaluation of Bone Formation by Osteogenic Protein 1 in the Baboon and Relative Efficacy of Bone–Derived Bone Morphogenetic Proteins Delivered by irradiated Xenogeneic Collagenous Matrices, 2000, pps. 1798–1809, Journal of Bone and Mineral Research, vol. 15, No. 9.

L. Callegaro et al., Hollow Fiber Immobilized L–Asparaginase: In Vivo and In Vitro Immunological Studies, 1983, pps. 91–96, The International Journal of Artificial Organs, vol. 6, No. 2.

G. Campalani et al., Aortic Valve Replacement With Frozen Irradiated Homografts, 1989, pps. 558–561, Eur. J. Cardio–thoracic Surgery, vol. 3.

David T. Cheung et al., The Effect of γ–Irradiation on Collagen Molecules, Isolated α–chains, and Crosslinked Native Fibers, 1990, pps. 581–589, Journal of Biomedical Materials Research, vol. 24.

David J. Cohen et al., The Fate of Aortic Valve Homografts 12 to 17 Years After Implantation, Mar. 1988, pps. 482–484, Chest, vol. 93, No. 3.

A.G. Churchalin et al., Clinical Immunosorbents Basing On Space–Network Polymers, 1998, pps. 1524–1529, All Union Research Institute of Chemical Reagents and Chemicals of Special Purity, Moscow.

P. De Deyne et al., Some Effects of Gamma Irradiation on Patellar Tendon Allografts, 1991, pps. 51–62, Connective Tissue Research, vol. 27.

R.I. Vaida et al., Structural–Functional Peculiarities of Myocardial Capillaries After Resection of the Lungs, Oct. 21, 1986, pps. 68–73.

R. Guidoin et al., A Compound Arterial Prosthesis: The Importance of the Sterilization Procedure on the Healing and Stability of Albuminated Polyester Grafts, Mar. 1985, pps. 122–128, Biomaterials, vol. 6.

Ph. Hernigou et al., Radiation Sterilization of Bone and the HIV Virus, 1993, pps. 445–451, Revue de Chirurgie Orthopedique, vol. 79.

Hsing–Wen Sung et al., Effects of Various Chemical Sterilization Methods on the Crosslinking and and Enzymatic Degradation Characteristics of an Epoxy–Fixed Biological Tissue, Dec. 1996, pps. 376–383, Sterilization of Biological Tissues.

James R. Malm et al., An Evaluation of Aortic Valve Homografts Sterilized by Electron Beam Energy, Oct. 1967, pps. 471–477, Journal of Thoracic and Cardiovascular Surgery, vol. 54, No. 4.

James R. Malm et al., Results of Aortic Valve Replacement Utilizing Irradiated Valve Homografts, pps. 740–747, Annals New York Academy of Sciences, prior art.

W. Oh et al., Mitral Valve Replacement With Preserved Cadaveric Aortic Homografts, May 1973, pps. 712–721, The Journal of Thoracic and Cardiovascular Surgery, vol. 65, No. 5.

K. Pietrucha, New Collagen Implant as Dural Substitute, Apr. 1991, pps. 320–323, Biomaterials, vol. 12.

Robert Sullivan et al., Inactivation of Thirty Viruses by Gamma Radiation, Jul. 1971, pps. 61–65, Applied Microbiology, vol. 22, No. 1.

D. Tylman, Mechanical Character of Liofilized and Sterilized by Gamma–Rays Bone Tissue, 1996, pps. 229–234, Chirurgia Narzadow Ruchu I, Ortopedia Polska.

W. Welch, A Comparative Study of Different Methods of Processing Aortic Homografts, 1969, pps. 746–749, Thorax, vol. 24.

J.M. White et al., Sterilization of Teeth by Gamma Radiation, Sep. 1994, pps. 1560–1567, J. Dent. Res., vol. 73, No. 9.

Boon–Seng Wong et al., Copper Refolding of Prior Protein, 2000, pps. 1217–1224, Biochemical and Biophysical Research Communications, vol. 276.

Boon–Seng Wong et al., Differential Contribution of Superoxide Dismutase Activity by Prior Protein in Vivo, 2000, pps. 136–139, Biochemical and Biophysical Research Communications, vol. 273.

Boon–Seng Wong et al., Prion Disease: A Loss of Antioxidant Function? 2000, pps. 249–252, Biochemical and Biophysical Research Communications, vol. 275.

D.E. Wyatt et al., Is There Life After Irradiation? Part I: Inactivation of Biological Contaminants, Jun. 1993, pps. 34–39, BioPharm.

Qi Zhang et al., Ethylene Oxide Does Not Extinguish the Osteoinductive Capacity of Demineralized Bone, 1997, pps. 104–108, Acta Orthop Scand, vol. 68, No. 2.

Yongxing Zhang et al., A Comprehensive Study of Physical Parameters, Biomechanical Properties and Statistical Correlations of Iliac Crest Bone Wedges Used in Spinal Fusion Surgery, 1994, pps. 304–308, Spine, vol. 19, No. 3.

License Agreement and procedures for Gamma Irradiation of Blood Products, Jun. 22, 1993, pps. 1–18, Dept. of Health & Human Services, Food and Drug Administration.

M.F. Alladine et al., γ–Radiation Damage to Starr–Edwards Valves, Mar. 16, 1998, pp. 68, The Lancet, Letters to the Editor.

Ch. Baquey et al., Radiosterilization of Albuminated Polyester Prostheses, May 1987, pps. 185–189, Biomaterials, vol. 8.

Edward H. Bedrossian, Jr., HIV and Banked Fascia Lata, 1991, pps. 284–288, Ophthalmic Plastic and Reconstructive Surgery, vol. 7, No. 4.

Liu Bingci, Mouse Antibody Response Following Repetitive Injections of Gamma–Irradiated Human Placenta Collagen, Jun. 1994, pps. 100–103, Chinese Medical Sciences Journal, vol. 9, No. 2.

A.A. Belov et al., The Influence of γ–Radiation on Enzyme Activity of Collalitin in the Process of Storage, Dec. 7, 1989, pps. 519–521, All–Union Research Institute of Textile and Haberdashery Industry, Moscow.

R.G. Burwell, The Fate of Freeze–Dried Bone Allografts, Jun. 1976, pps. 95–111, Transplantation Proceedings, vol. VII, No. 2, Supplement 1.

Jan Parizek et al., Duraplasty With Pretreated Freeze–Dried Sterilized Human Dura Mater, 1990, pps. 135–143, Sbor. ved. Praci LF UK Hradee Kralove, vol. 33.

Jan Parizek et al., Ovine Pericardium: A New Material For Duraplasty, 1996, pps. 508–513, J. Neurosurg., vol. 84.

Patel et al., Effect of Gamma Radiation and Ethylene Oxide on Papain, 1979, pps. 81–83, Indian. J. Pharm. Sci., vol. 41, No. 2.

L.V. Polezhaeu et al., Repair of Cranial Defects With Regenerating Bone in Grafting Gamma–Irradiated Bone Filings, pps. 57–60, prior art.

Pollard, The Effect of Ionizing Radiation on Viruses, pps. 65–71, prior art.

Donald J. Prolo et al., Composite Autogeneic Human Cranioplasty: Frozen Skull Supplemental With Fresh Iliac Corticocancellous Bone, Dec. 1984, pps. 846–851, Neurosurgery, vol. 15, No. 6.

Donald J. Prolo et al., Superior Osteogenesis in Transplanted Allogeneic Canine Skull Following Chemical Sterilization, Aug. 1982, pps. 230–242, Clinical Orthopaedics and Related Research, No. 168.

Elena Quaglio et al., Copper Converts the Cellular Prion Protein Into a Protease–resistant Species That Is Distinct From the Scrapie Isoform, Apr. 6, 2001, pps. 11432–11438, The Journal of Biological Chemistry, vol. 276, No. 14.

T.J. Rasmussen et al., The Effects of 4 Mrad of Gamma–Irradiation on the Initial Mechanical Properties of Bone–Patellar Tendon–Bone Grafts, 1994, pps. 188–197, The Journal of Arthroscoic and Related Surgery, vol. 10, No. 2.

Brian D. Reid, The Sterways Process: A New Approach to Inactivating Viruses Using Gamma Radiation, 1998, pps. 125–130, Biologicals, vol. 26.

S.C. Roe et al., The Effect of Gamma Irradiation on a Xenograft Tendon Bioprothesis, 1992, pps. 149–154, Clinical Materials, vol. 9.

Robert G. Rohwer, Estimation of Scrapie Nucleic Acid MW From Standard Curves for Virus Sensitivity to Ionizing Radiation, Mar. 27, 1986, pp. 381, Nature, vol. 320, No. 6060.

Robert G. Rohwer, Scrapie Infectious Agent is Virus–like in Size and Susceptibility to Inactivation, Apr. 12, 1984, pps. 658–662, Nature, vol. 308.

R.G. Rohwer, The Scrapie Agent: A Virus by Any Other Name, pps. 195–232, Current Topics in Microbiology and Immunology, vol. 172, prior art.

Robert G. Rohwer et al., Scrapie–Virus or Viroid, The Case For a Virus, pps. 335–355, Laboratory of Central Nervous System Studies, National Institutes of Neurological and Communicative Disorders and Stroke, National Institutes of Health, prior art.

Robert G. Rohwer, Virus–Like Sensitivity of the Scrapie Agent to Heat Inactivation, Feb. 10, 1984, pps. 600–602, Science, vol. 223.

E.S. Kempner et al., Size Determination of Enzymes by Radiation Inactivation, 1979, pps. 2–10, Analytical Biochemistry, vol. 92.

L. Kerboull et al., In Vitro Study of the Influence of Avrious Conservation Methods on the Mechanical Properties of Patellar Tendon Allografts, 1991, pps. 751–762, Chirurgie, vol. 117.

A.D. Kitchen, Effects of Gamma Irradiation on the Human Immunodeficiency Virus and Human Coagulation Proteins, 1989, pps. 223–229, Vox Sang, vol. 56.

Andrezej Komender et al., Some Biological Properties of Bovine Trypinized Fascia Xenografts, 1981, pps. 485–489, Archivum Immunologiae et Therapiae Experimentalis, vol. 29.

Andrezej Komendar et al., Some Biological Properties of Preserved Bovine Fascia Enrighed With Pulverized Calf Cartilage, 1984, pps. 211–219, Archivum Immunologiae et Therapiae Experimentalis, vol. 32.

J.F. Kouvalchouk et al., The Use of Sterilized Bone Allografts in Reconstruction After Tumour Resection, 1986, pps. 393–401, Revue de Chirurgie Orthopedique, vol. 72.

Raymond Latarjet, Inactivation of the Agents of Scrapie, Creutzfeldt–Jakob Disease, and Kuru by Radiations, 1979, pps. 387–407, Slow Transmissible Diseases of the Nervous System, vol. 2.

R. Latarjet et al., Inactivation of the Scrapie Agent by Near Monochromatic Ultraviolet Light, Sep. 26, 1970, pps. 1341–1343, Nature, vol. 227.

Douglas C. Lee et al., A Direct Relationship Between the Partitioning of the Pathogenic Prion Protein and Transmissible Spongiform Encephalopathy Infectivity During the Purification of Plasma Proteins, Apr. 2001, pps. 449–455, Transfusion, vol. 41.

Susan F. Leitman, Use of Blood Cell Irradiation in the Prevention of Posttransfusion Graft–vs–Host Disease, 1989, pps. 219–232, Transfus. Sci., vol. 10.

Linberg et al., Irradiated Homologous Cartilage For Orbital Reconstruction, Jul. 1980, pps. 457–462, Ophthalmic Surgery, vol. 11.

Sandra McDowell, Irradiated Cartilage, Spring 1988, pps. 14–15, Plastic Surgical Nursing.

A. Maeda et al., Effects of Solvent Preservation With or Without Gamma Irradiation on the Material Properties of Canine Tendon Allografts, 1993, pps. 181–189, Journal of Orthopaedic Research, vol. 11.

Akira Maeda et al., Solvent–dried and Gamma–irradiated Tendon Allografts in Rats, Jul. 1998, pps. 731–736, The Journal of Bone and Joint Surgery, vol. 80–B, No. 4.

S. Malawski et al., The Use of Dry–Freezed Bone Grafts Sterilized by Gamma Rays in Orthopaedic Surgery, 1969, pps. 61–68, Chir. Narz. Ruchu Ortop.

Linda Marton et al., Disinfection and Inactivation of the Human T. Lymphotrogic Virus Type III/Lymphadenopathy–Associated Virus, Aug. 1985, pps. 499–403, The Journal of Infectious Diseases, vol. 151, No. 2.

S.I. Miekka et al., New Methods for Inactivation of Lipid–enveloped and Non–enveloped Viruses, 1998, pps. 402–408, Haemophilia, vol. 4.

Ken Nakata et al., Reconstruction of the Lateral Ligaments of the Ankle Using Solvent–dried and Gamma–Irradiated Allogeneic Fascia Lata, May 2000, pps. 579–582.

Maria Esther Martinez Pardo et al., Clinical Application of Amniotic Membranes on a Patient With Epidermolysis Bullosa, 1999, pps. 68–73, Annals of Transplantation, vol. 4, No. 3–4.

J.R.P. Gibbons et al., Gamma Ray Sterilisation of Homograft Valves, 1969, pps. 353–358, Bulletin De La Societe Internationale De Chirugie, No. 3.

M.J. Goertzen et al., Anterior Cruciate Ligament Reconstruction Using Cryopreserved Irradiated Bone–ACL–Bone–Allograft Transplants, 1994, pps. 150–157, Knee Surgery Sports Traumatology Arthroscopy, vol. 2.

Slawomir Gregorczyn et al., Strength of Lyophilized and Irradiated Cortical Bone of the Human Femur, 1995, pps. 129–133, Chir. Narz. Ruchu Ortop. Pol., Lx 2.

D.A. Haig, Further Studies on the Inactivation of the Scrapie Agent by Ultraviolet Light, 1969, pps. 455–457, J. Gen. Virol., vol. 5.

F.W. Hehrlein et al., Biochemische Veränderungen an Heterologen Aortenklappentransplantaten nach Anwendung Verschiedener Sterilisationsverfahren, pps. 1183–1185, Langenbecks Arch. Chir., Bd. 325 (Kongrebericht) (English Summary found at p. 1183), prior art.

F.W. Hehrlein et al., Morphologische Utersuchungen an Heterologen Herzlappentransplantaten Unter Verschiedenen Sterilisationsbedingungen, pps. 244–251 (English Summary found at p. 250), prior art.

H. Hiemstra et al., Inactivation of Human Immunodeficiency Virus by Gamma Radiation and its Effect on Plasma and Coagulation Factors, 1991, pps. 32–39, Transfusion, vol. 31, No. 1.

Richard Hinton et al., A Biomechanical Analysis of Solvent–dehydrated and Freeze–Dried Human Fascia Lata Allografts, 1992, pps. 607–612, The American Journal of Sports Medicine, vol. 20, No. 5.

B. Horowitz et al., Inactivation of Viruses in Labile Blood Derivatives, II. Physical Methods, 1985, pps. 523–527, Transfusion, vol. 25, No. 6.

M. Horowitz, Sterilization of Homograft Ossicles by Gamma Radiation, Nov. 1979, pps. 1087–1989, The Journal of Laryngology and Otology, vol. 93.

Carol House et al., Inactivation of Viral Agents in Bovine Serum by Gamma Irradiation, 1990 pps. 736–740, Can. J. Microbiol., vol. 36.

Shinichiro Ijiri et al., Effect of Sterilization on Bone Morphogenetic Protein, 1994, pps. 628–636, Journal of Orthopaedic Research, vol. 12.

A.S. Immaliev et al., Biological Properties of Bone Tisue Conserved in Plastic Material and Sterilized With Gamma Rays, 1974, pps. 129–135, ACTA, Chirurgiae Plasticae, vol. 16, No. 3.

A. Ingegneri et al., An 11–Year Assessment of 93 Flash–frozen Homograft Valves in the Aortic Position, 1979, pps. 304–307, Thorac. Cardiovasc. Surgeon, vol. 27.

J. Jerosch et al., A New Technique for Bone Sterilization, 1989, pps. 117–120, Biomedizinische Technik, Band 34, Heft 5.

J. Jerosch et al., Influence of Different Rehydration Periods on the Stability and the Water Content of Bone Allografts After Lyophilization, Gamma–Irradiation, and Lipid Extraction, 1994, pps. 335–341, Z. Orthop., vol. 132.

J.D. Keathley et al., Is There Life After Irradiation? Part 2: Gamma–Irradiated FBS in Cell Culture Jul./Aug. 1993, pps. 46–52, BioPharm.

P. Brown, The Risk of Blood–Borne Creutzfeldt–Jakob Disease, 1999, pps. 53–59, Advances in Transfusion Safety Dev. Biol. vol. 102.

P. Brown et al., Further Studies on Blood Infectivity in an Experimental Model of Transmissible Spongiform Encephalopathy, With an Explanation of Why Blood Components Do Not Transmit Cruetzfeldt–Jakob Disease in Humans, Nov./Dec. 1999, pps. 1169–1178, Transfusion, vol. 39.

Paul Brown et al., Effect of Chemicals, Heat, and Histopathologic Processing on High–Infectivity Hamster–Adapted Scrapie Virus, May 1982, pps. 683–687, The Journal of Infectious Diseases, vol. 145, No. 5.

P. Brown et al., The Distribution of Infectivity in Blood Components and Plasma Derivatives in Experimental Models of Transmissible Spongiform Encephalopathy, Sep. 1998, pps. 810–816, Transfusion, vol. 38.

D.G. Campbell et al., Sterilization of HIV With Irradiation: Relevance to Infected Bone Allografts, 1999, pps. 517–521, Aust. N.Z.J. Surg., vol. 69.

Ernest U. Conrad et al., Transmission of the Hepatitis–C Virus by Tissue Transplantation, Feb. 1995, pps. 214–224, The Journal of Bone and Joint Surgery, vol. 77–A, No. 2.

A.S. Dagli, Correction of Saddle Nose Deformities by Coral Implantation, 1997, pps. 274–276, Eur. Arch. Otorhinolaryngol, vol. 254.

Defeng et al., Sterilization of Silver–Acidum Pipemedicum Skin for the Treatment of Burns by Radioactive Cobalt–60–.Gamma.–Ray, 1995, pps. 406 (Abstract).

P. Di Simplicio et al., The Reactivity of the SH Group of Bovine Serum Albumin With Free Radicals, 1991, pps. 253–262, Free Rad. Res. Comms., vol. 14, No. 4.

R.J. Donnelly et al., Gamma–radiation of Heart Valves at 4° C; A Comparative Study Using Techniques of Histochemistry and Electron and Light Microscopy, 1973, pps. 95–101, Thorax, vol. 28.

Duane C. Eichler et al., Radiation Inactivation Analysis of Enzymes, Jul. 15, 1997, pps. 9433–9346, The Journal of Biological Chemistry, vol. 262, No. 20.

Luanne H. Elliott et al., Inactivation of Lassa, Marburg and Ebola Viruses by Gamma Irradiation, Oct. 1982, pps. 704–708, Journal of Clinical Microbiology, vol. 16, No. 4.

Bradley M. Fideler et al., Gamma Irradiation: Effects on Biomechanical Properties of Human Bone–Patellar Tendon–Bone Allografts, 1995, pps. 643–646, American Journal of Sports Medicine, vol. 23, No. 5.

Bradley M. Fideler et al., Effects of Gamma Irradiation on the Human Immunodeficiency Virus, Jul. 1994, The Journal of Bone and Joint Surgery, vol. 76–A, No. 7.

Fields et al., Susceptibility of Scrapie Agent to Ionizing Radiation, Apr. 5, 1969, pps. 90–91, Nature, vol. 222.

M.J. Gibbons et al., Effects of Gamma Irradiation on the Initial and Mechanical and Material Properties of Goat Bone–Patellar Tendon–Bone Allografts, 1991, pps. 209–218, J. Orthop Res, vol. 9, No. 2.

Seymour S. Block, Disinfection, Sterilization, and Preservation, Fundamental Principles of Activity Principles of Antimicrobial Activity, Fourth Edition, 1991, pps. 31–33.

A.J.J.C. Bogers et al., Long–Term Results of the Gamma–Irradiation–Preserved Homograft Monocusp for Transannular Reconstruction of the Right–Ventricular Outflow Tract in Tetralogy of Fallot, 1994, pps. 337–330, Thorac. Cardiovasc. Surgeon, vol. 42.

David R. Brown et al., Antioxidant Activity Related to Copper Binding of Native Prion Protein, 2001 pps. 69–76, Journal of Neurochemistry, vol. 76.

R.H. Bassin et al., Abrogation of Fv–1$^b$Restriction With Murine Leukemia Viruses Inactivated by Heat or by Gamma Irradiation, May 1978, pps. 306–315, Journal of Virology, vol. 26, No. 2.

Guy Beauregard et al., Temperature Dependence of the Radiation Inactivation of Proteins, 1985, pps. 117–120, Analytical Biochemistry, vol. 150.

Sandra Blakeslee, Tight Rules on Use of Organs Do Not Apply to Tissues, Jan. 20, 2002, The New York Times Newspaper.

S.R. Aparicio et al., Light and Electron Microscopy Studies on Homograft and Heterograft Heart Valves, 1975, pps. 174–162, J. Path, vol. 115.

J. Baksa et al., The Use of Pig's Skin (xenograft) for the Treatment of Burns, 1976, pps. 138–145, Magyar Traumatologin, vol. 19.

Michael L. Baldwin et al., Irradiation of Blood Components, 1992, pps. 10–78, American Association of Blood Banks.

Tikvah Alper et al., Protection by Anoxia of the Scrapie Agent and Some DNA and RNA Viruses Irradiated as Dry Preparations, 1968, pps. 157–166, J. Gen. Virol., vol. 3.

Tikvah Alper et al., Does the Agent of Scrapie Replicate Without Nucleic Acid? May 20, 1967, pps. 764–766, Nature, vol. 214.

Tikvah Alper et al., The Scrapie Agent: Evidence Against its Dependence For Replication on Intrinsic Nucleic Acid, 1978, pps. 503–516, J. Gen. Virol., vol. 41.

AABB FDA Liaison Meeting, ABC Newsletter, Dec. 12, 1997, pp. 14.

Ozan Akkus et al., Fracture Resistance of Gamma Radiation Sterilized Cortical Bone Allografts, 2001, pps. 927–934, Journal of Orthopaedic Research, vol. 19.

Tikvah Alper et al., The Exceptionally Small Size of the Scrapie Agent, 1966, pps. 278–284, Biochemical and Biophysical Research Communications, vol. 22, No. 3.

* cited by examiner

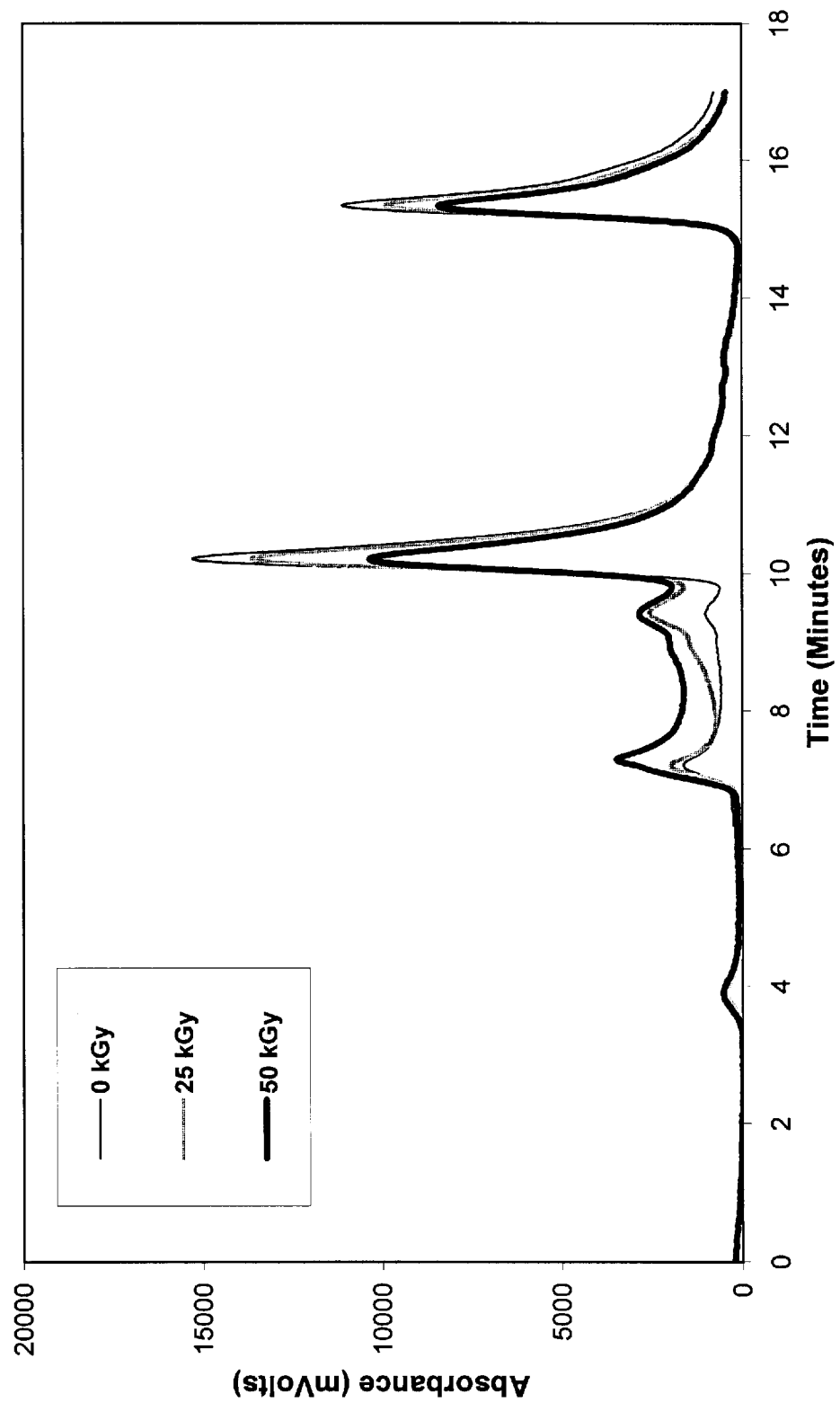

METHODS FOR STERILIZING BIOLOGICAL MATERIALS

FIELD OF THE INVENTION

The present invention relates to methods for sterilizing biological materials to reduce the level therein of one or more biological contaminants or pathogens, such as prions, responsible for the disease states known as transmissible spongiform encephalopathies (TSEs) in mammals. The present invention particularly relates to methods of sterilizing biological materials with irradiation.

BACKGROUND OF THE INVENTION

Many biological materials that are prepared for human, veterinary, diagnostic and/or experimental use may contain unwanted and potentially dangerous biological contaminants or pathogens, such as viruses, bacteria, nanobacteria, yeasts, molds, mycoplasmas, ureaplasmas, prions and parasites. Consequently, it is of utmost importance that any biological contaminant or pathogen in the biological material be inactivated before the product is used. This is especially critical when the material is to be administered directly to a patient, for example in blood transfusions, blood factor replacement therapy, organ transplants and other forms of human therapy corrected or treated by intravenous, intramuscular or other forms of injection. This is also critical for the various biological materials that are prepared in media or via culture of cells or recombinant cells which contain various types of plasma and/or plasma derivatives or other biologic materials and which may be subject to mycoplasma, prion, bacterial and/or viral contaminant or pathogens.

Most procedures for producing biological materials have involved methods that screen or test the biological materials for one or more particular biological contaminants or pathogens rather than removal or inactivation of the contaminant(s) or pathogen(s) from the material. Materials that test positive for a biological contaminant or pathogen are merely not used. Examples of screening procedures include the testing for a particular virus in human blood from blood donors. Such procedures, however, are not always reliable and are not able to detect the presence of certain viruses, particularly in very low numbers. This reduces the value or certainty of the test in view of the consequences associated with a false negative result. False negative results can be life threatening in certain cases, for example in the case of Acquired Immune Deficiency Syndrome (AIDS). Furthermore, in some instances it can take weeks, if not months, to determine whether or not the material is contaminated. Therefore, it would be desirable to apply techniques that would kill or inactivate contaminants or pathogens during and/or after manufacturing the biological material.

Moreover, to date, there is no reliable test or assay for identifying prions within a biological material that is suitable for screening out potential donors or infected material. This serves to heighten the need for an effective means of destroying priors within a biological material, while still retaining the desired activity of that material.

In conducting experiments to determine the ability of technologies to inactivate viruses, the actual viruses of concern are seldom utilized. This is a result of safety concerns for the workers conducting the tests, and the difficulty and expense associated with the containment facilities and waste disposal. In their place, model viruses of the same family and class are used.

In general, it is acknowledged that the most difficult viruses to inactivate are those with an outer shell made up of proteins, and that among these, the most difficult to inactivate are those of the smallest size. This has been shown to be true for gamma irradiation and most other forms of radiation as these viruses' diminutive size is associated with a small genome. The magnitude of direct effects of radiation upon a molecule are directly proportional to the size of the molecule, that is the larger the target molecule, the greater the effect. As a corollary, it has been shown for gamma-irradiation that the smaller the viral genome, the higher the radiation dose required to inactive it.

Among the viruses of concern for both human and animal-derived biological materials, the smallest, and thus most difficult to inactivate, belong to the family of Parvoviruses and the slightly larger protein-coated Hepatitis virus. In humans, the Parvovirus B19, and Hepatitis A are the agents of concern. In porcine-derived materials, the smallest corresponding virus is Porcine Parvovirus. Since this virus is harmless to humans, it is frequently chosen as a model virus for the human B19 Parvovirus. The demonstration of inactivation of this model parvovirus is considered adequate proof that the method employed will kill human B19 virus and Hepatitis A, and by extension, that it will also kill the larger and less hardy viruses such as HIV, CMV, Hepatitis B and C and others.

More recent efforts have focussed on methods to remove or inactivate contaminants in the products. Such methods include heat treating, filtration and the addition of chemical inactivants or sensitizers to the product.

Heat treatment requires that the product be heated to approximately 60° C. for about 70 hours which can be damaging to sensitive products. In some instances, heat inactivation can actually destroy 50% or more of the biological activity of the product.

Filtration involves filtering the product in order to physically remove contaminants. Unfortunately, this method may also remove products that have a high molecular weight. Further, in certain cases, small viruses may not be removed by the filter.

The procedure of chemical sensitization involves the addition of noxious agents which bind to the DNA/RNA of the virus and which are activated either by UV or other radiation. This radiation produces reactive intermediates and/or free radicals which bind to the DNA/RNA of the virus, break the chemical bonds in the backbone of the DNA/RNA, and/or cross-link or complex it in such a way that the virus can no longer replicate. This procedure requires that unbound sensitizer is washed from products since the sensitizers are toxic, if not mutagenic or carcinogenic, and cannot be administered to a patient.

Irradiating a product with gamma radiation is another method of sterilizing a product. Gamma radiation is effective in destroying viruses and bacteria when given in high total doses (Keathly et al., "Is There Life After Irradiation? Part 2," *BioPharm* July–August, 1993, and Leitman, "USe of Blood Cell Irradiation in the Prevention of Post Transfusion Graft-vs-Host Disease," *Transfusion Science* 10:219–239 (1989)). The published literature in this area, however, teaches that gamma radiation can be damaging to radiation sensitive products, such as blood, blood products, protein and protein-containing products. In particular, it has been shown that high radiation doses are injurious to red cells, platelets and granulocytes (Leitman). U.S. Pat. No. 4,620,908 discloses that protein products must be frozen prior to irradiation in order to maintain the viability of the protein product. This patent concludes that "[i]f the gamma irradiation were applied while the protein material was at, for example, ambient temperature, the material would be also completely destroyed, that is the activity of the material would be rendered so low as to be virtually ineffective". Unfortunately, many sensitive biological materials, such as monoclonal antibodies (Mab), may lose viability and activity if subjected to freezing for irradiation purposes and then thawing prior to administration to a patient.

Recently, public attention has been attracted to the problem of human and animal products containing biological contaminants or pathogens that cause transmissible spongiform encephalopathies (TSEs) in mammals. TSEs cause inflammation and characteristic spongelike holes in the delicate membranes surrounding brain cells, which results in loss of coordination, dementia, and, eventually, death. Perhaps the best-known TSE is bovine spongiform encephalopathy (BSE), more popularly known as mad cow disease. BSE made headlines in 1996 when about a million cattle in the United Kingdom became infected with the disease when they ate feed made from the processed animal parts of infected sheep, pigs, and chickens. Ingestion of the infected cow meat caused about 20 people in Britain to develop an unusual form of Creutzfeldt-Jakob disease. Other TSEs include kuru, a rare disease contracted by natives of New Guinea who ate the infected brains of their dead relatives during ritual cannibalism, and scrapie, which affects sheep and goats and is so named because diseased sheep sometimes scrape off their own wool.

A prion (a shortened term for proteinaceous infectious particle) is believed to be a small protein associated with TSEs in cows, sheep, humans, and other mammals. Prions appear to be a mutated form of a normal protein. The normal protein (PrP) is found on the surface of nerve cells in the brain, white blood cells, muscle cells, and cells of many other tissues. The role of the normal protein is not yet understood, but its structure has been elucidated. A hundred times smaller than the smallest virus, the normal protein is composed of 208 amino acids twisted into three $\alpha$-helices, from one of which extends a floppy tail of 97 amino acids. The mutated form of the protein ($PrP^{sc}$) is built of the same amino acids. Instead of $\alpha$-helices, however, the mutated protein is folded into $\beta$-sheets.

The high level of the mutated protein in neural and other tissue of an infected individual makes transmission of infection to another individual more likely, particularly if the non-infected individual consumes the tissue(s) of the infected individual. In this manner, infection with TSEs has occurred in animals fed processed tissue(s) obtained from infected animals, in humans who consumed tissue(s) obtained from infected animals or humans, and in humans who received tissue(s) or tissue extracts therapeutically and the tissue(s) had been donated by an infected individual.

In 1967, Tikvah Alper and her colleagues at the Hammersmith Hospital in London extracted brain tissue from scrapie-infected sheep. This processed tissue was then injected into healthy sheep to see if the disease would be transmitted. The healthy sheep contracted scrapie, indicating that the infectious agent was in the diseased brain tissue and that it could reproduce in healthy animals to cause disease. Alper then exposed similar scrapie-infected tissue extracts to ultraviolet radiation, which normally destroys DNA and RNA, and found that the extracts maintained their ability to transmit scrapie. The resistance of the infectious agent to ultraviolet radiation suggested that neither a virus nor bacteria, both of which reproduce through nucleic acids, caused the disease.

In the early 1980s, Stanley B. Prusiner at the University of California, San Francisco concluded that proteins were responsible for TSEs based on evidence that tissue extracts from scrapie-infected animals no longer caused disease after exposure to treatments known to destroy proteins. It was suggested that the mutated protein causes disease when it contacts the normal protein and triggers part of it to switch from the normal $\alpha$-helical form to the mutant $\beta$-pleated form. A chain reaction would follow, resulting in the cluster of tangled, nonfunctional plaques found in the brains of animals that die from TSEs.

Not all scientists and doctors agree, however, that TSEs are transmitted by an infectious protein. It is still considered possible that the infectious agent responsible for TSEs is a small virus, either alone or in combination with the prion protein or another, as yet unidentified, cofactor. For the purposes of the present invention, the actual nature of the agent(s) responsible for TSEs is unimportant, so long as the agent(s) are rendered inactive, i.e. non-infectious, by the processes of the present invention, while retaining an adequate level of the activity of the treated biological material.

There therefore remains a need for methods of sterilizing compositions of biological materials that are effective for reducing or preventing the occurrence of TSEs without an adverse effect on the biological material(s).

SUMMARY OF THE INVENTION

Accordingly, it is an object of the present invention to provide methods of sterilizing biological materials by reducing the level of prions, and, optionally, other active biological contaminants or pathogens, without adversely affecting the material. Other objects, features and advantages of the present invention will be set forth in the detailed description of preferred embodiments that follows, and in part will be apparent from the description or may be learned by practice of the invention. These objects and advantages of the invention will be realized and attained by the compositions and methods particularly pointed out in the written description and xclaims hereof.

In accordance with these and other objects, a first embodiment of the present invention is directed to a method for sterilizing a biological material that is sensitive to radiation comprising irradiating the biological material with radiation for a time effective to sterilize the material at a rate effective to sterilize the material and to protect the material from radiation.

Another embodiment of the present invention is directed to a method for sterilizing a biological material that is sensitive to radiation comprising: (i) adding to a biological material at least one stabilizer in an amount effective to protect the biological material from radiation; and (ii) irradiating the biological material with radiation at an effective rate for a time effective to sterilize the material.

Another embodiment of the present invention is directed to a method for sterilizing a biological material that is sensitive to radiation comprising: (i) reducing the residual solvent content of a biological material to a level effective to protect the biological material from radiation; and (ii) irradiating the biological material with radiation at an effective rate for a time effective to sterilize the biological material.

Another embodiment of the present invention is directed to a method for sterilizing a biological material that is sensitive to radiation comprising: (i) reducing the temperature of a biological material to a level effective to protect the biological material from radiation; and (ii) irradiating the biological material with radiation at an effective rate for a time effective to sterilize the biological material.

Another embodiment of the present invention is directed to a method for sterilizing a biological material that is sensitive to radiation comprising: (i) applying to the biological material a stabilizing process selected from the group consisting of: (a) reducing the residual solvent content of a biological material, (b) adding to the biological material at least one stabilizer, and (c) reducing the temperature of the biological material; and (ii) irradiating the biological material with radiation at an effective rate for a time effective to sterilize the biological material, wherein the stabilizing process and the rate of irradiation are together effective to protect the biological material from radiation.

Another embodiment of the present invention is directed to a method for sterilizing a biological material that is sensitive to radiation comprising: (i) applying to the biological material at least two stabilizing processes selected from the group consisting of: (a) reducing the residual solvent content of a biological material, (b) adding to the biological material at least one stabilizer, and (c) reducing the temperature of the biological material; and (ii) irradiating the biological material with radiation at an effective rate for a time effective to sterilize the biological material, wherein the stabilizing processes may be performed in any order and are together effective to protect the biological material from radiation.

The invention also provides a biological composition comprising at least one biological material and a least one stabilizer in an amount effective to preserve the biological material for its intended use following sterilization with radiation.

The invention also provides a biological composition comprising at least one biological material in which the residual solvent content has been reduced to a level effective to preserve the biological material for its intended use following sterilization with radiation.

The invention also provides a biological composition comprising at least one biological material and at least one stabilizer in which the residual solvent content has been reduced and wherein the amount of stabilizer and level of residual solvent content are together effective to preserve the biological material for its intended use following sterilization with radiation.

FIGS. 4A–4D are SDS-PAGE gels of human serum albumin following irradiation with various doses of gamma radiation.

FIGS. 5A–5D are HPSEC outputs of the same human serum albumin following irradiation with various doses of gamma radiation.

DETAILED DESCRIPTION OF THE PREFERRED EMBODIMENTS

A. Definitions

Unless defined otherwise, all technical and scientific terms used herein are intended to have the same meaning as is commonly understood by one of ordinary skill in the relevant art.

As used herein, the singular forms "a," "an," and "the" include the plural reference unless the context clearly dictates otherwise.

As used herein, the term "biological material" is intended to mean any substance derived or obtained from a living organism. Illustrative examples of biological materials include, but are not limited to, the following: cells; tissues; blood or blood components; proteins, including recombinant and transgenic proteins, and proetinaceous materials; enzymes, including digestive enzymes, such as trypsin, chymotrypsin, alpha-glucosidase and iduronodate-2-sulfatase; immunoglobulins, including mono and polyimmunoglobulins; botanicals; food and the like. Preferred examples of biological materials include, but are not limited to, the following: ligaments; tendons; nerves; bone, including demineralized bone matrix, grafts, joints, femurs, femoral heads, etc.; teeth; skin grafts; bone marrow, including bone marrow cell suspensions, whole or processed; heart valves; cartilage; corneas; arteries and veins; organs, including organs for transplantation, such as hearts, livers, lungs, kidneys, intestines, pancreas, limbs and digits; lipids; carbohydrates; collagen, including native, afibrillar, atelomeric, soluble and insoluble, recombinant and transgenic, both native sequence and modified; chitin and its derivatives, including NO-carboxy chitosan (NOCC); stem cells, islet of Langerhans cells and other cells for transplantation, including genetically altered cells; red blood cells; white blood cells, including monocytes; and platelets.

As used herein, the term "sterilize" is intended to mean a reduction in the level of one or more of the biological contaminants or pathogens found in the biological material being treated according to the present invention, wherein these biological contaminants or pathogens are responsible, alone or in combination, for one or more of the disease states known as transmissible spongiform encephalopathies (TSEs) in mammals. Generally, such a reduction in the level of the biological contaminant(s) or pathogen(s) is at least a 1 log reduction, usually at least a 2 log reduction, preferably at least a 3 log reduction, more preferably at least a 4 log reduction and most preferably at least a 4.5 log reduction in the level.

Illustrative examples of transmissible spongiform encephalopathies (TSEs) in mammals include, but are not limited to, the following: scrapie; transmissible mink encephalopathy; chronic wasting disease (generally observed in mule deer and elk); feline spongiform encephalopathy; bovine spongiform encephalopathy (mad cow disease); Creutzfeld-Jakob disease; Fatal Familial Insomnia; Gerstmann-Straeussler-Scheinker syndrome; kuru; and Alpers syndrome. These diseases are characterized by loss of motor control, dementia, paralysis wasting and eventually death, typically following pneumonia. Visible end results at post-mortem are non-inflammatory lesions, vacuoles, amyloid protein deposits and astrogliosis.

While not wishing to be bound to any particular theory as to the identity of the specific agent(s), infective or native, responsible for TSEs, such biological contaminants or pathogens may include one or more mammalian prion proteins (PrP), either in a normal $\alpha$-helical form (PrP) or a mutated $\beta$-sheet form ($PrP^{sc}$), or one or more small viruses or similar infective agents, such as virions or viroids, or a combination of two or more thereof. The determination as to whether a biological material has been "sterilized" according to the methods of the present invention is therefore assessed according to the occurrence of TSEs in recipients of the biological material being treated. Thus, according to the present invention, a biological material has been "sterilized" if there is a reduction in the occurrence of TSEs in recipients of the biological material, as measured, for example, by a reduction in the number of infections in a given population or a delay in the time-to-onset of the disease.

Figure 1:
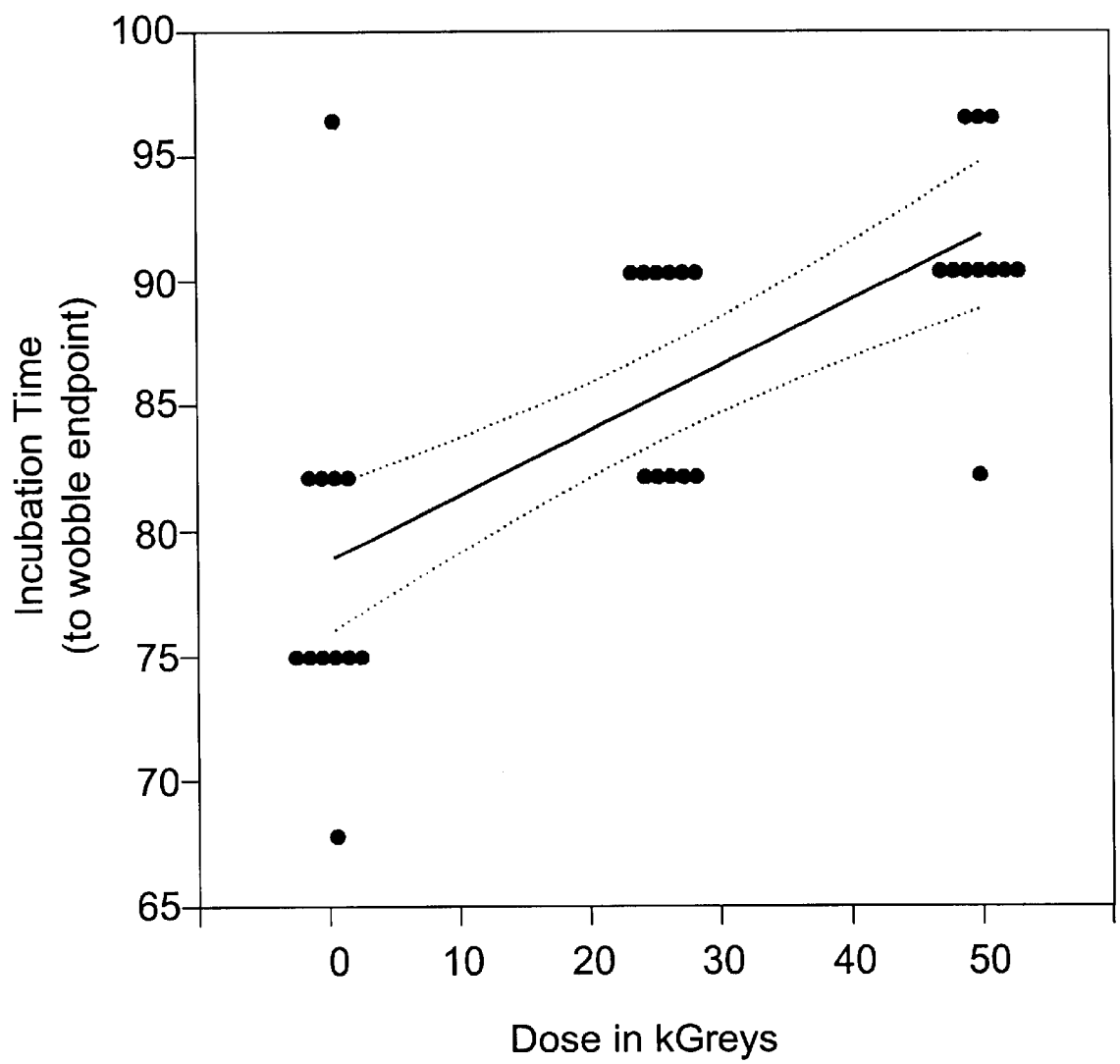
FIGS. 1–3 are graphs showing the date of onset of symptoms (ataxia/wobble, failure to rear and mortality, respectively) of animals infected with scrapie-spiked human serum albumin, with and without sterilization by various doses of gamma radiation.
Figure 2:
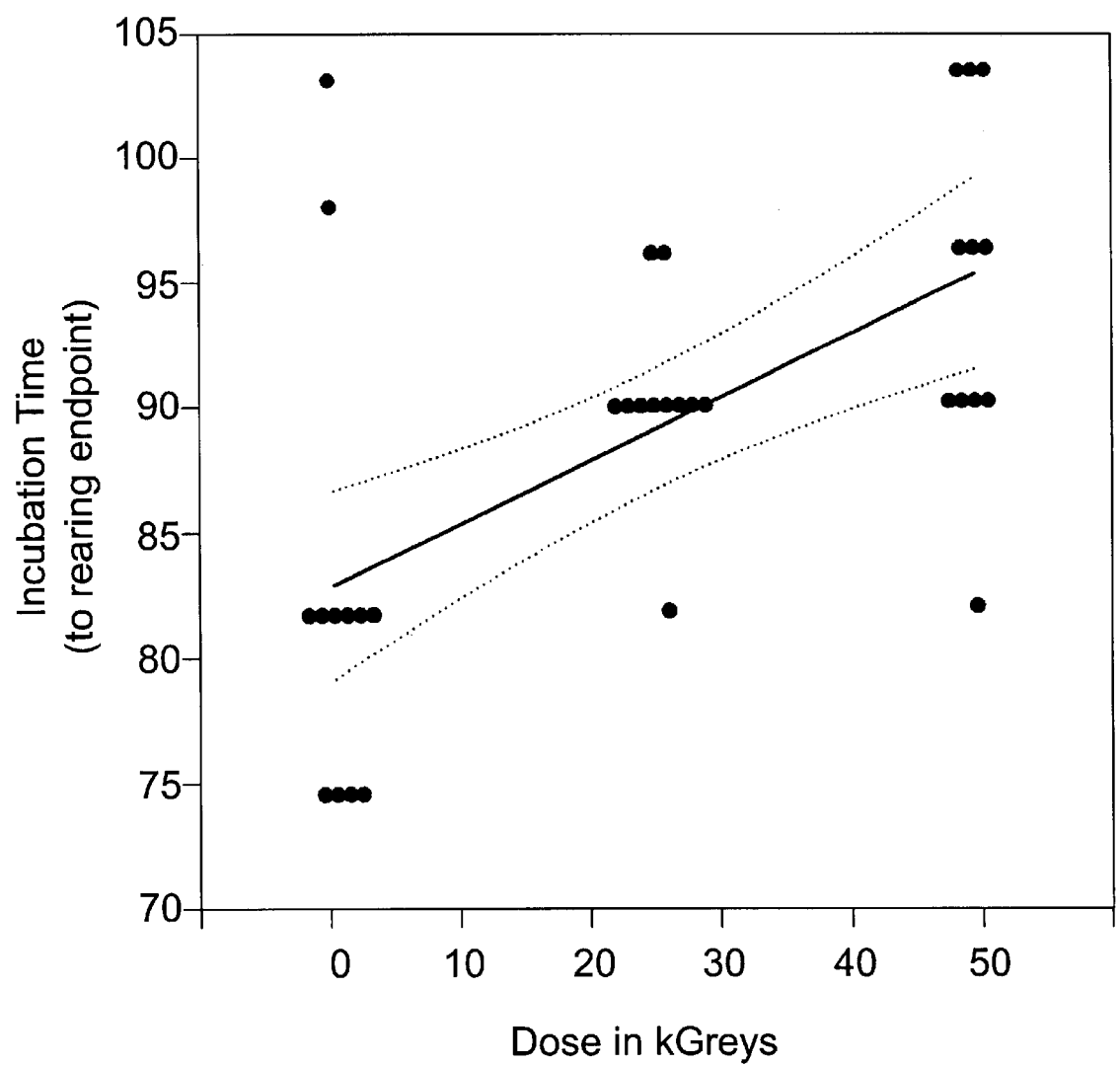
Figure 3:
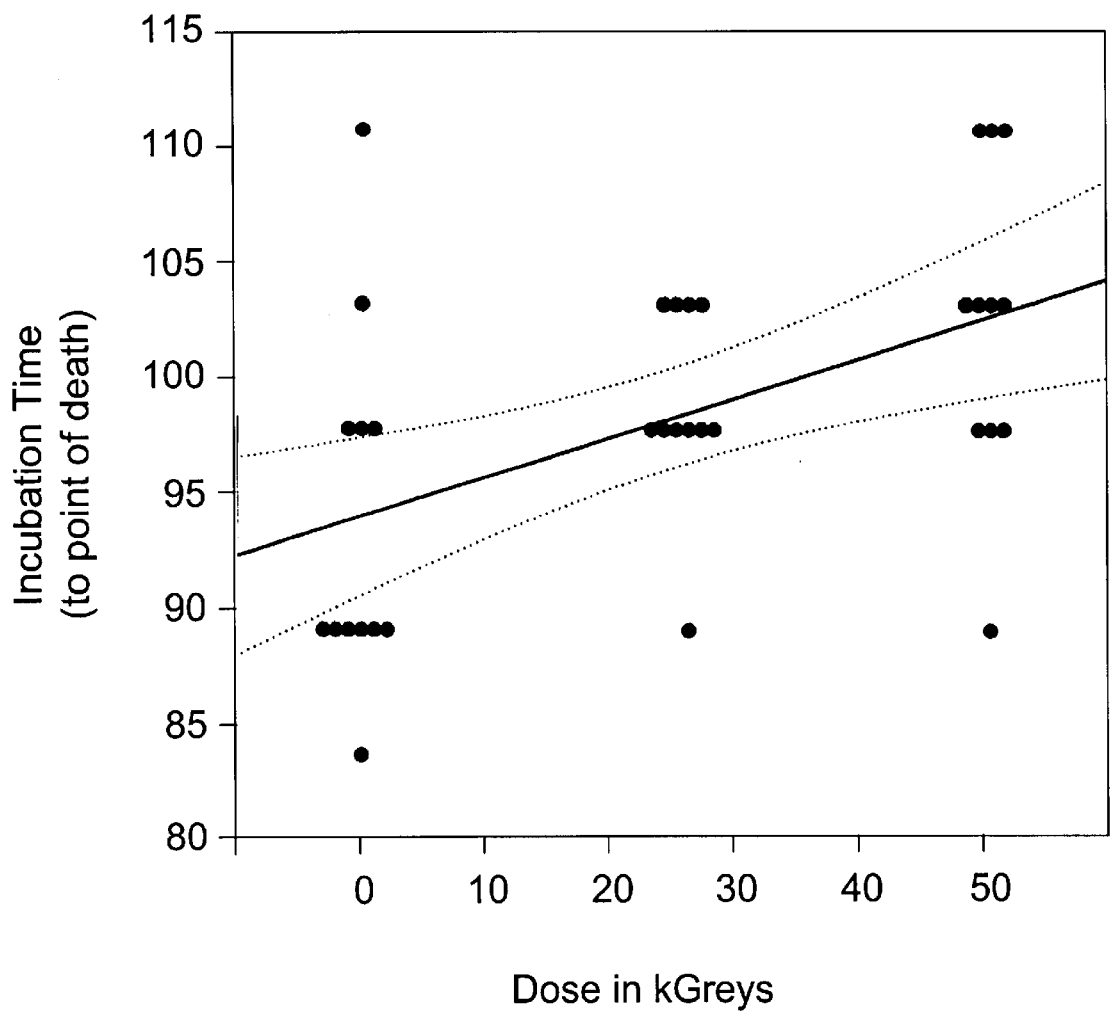

As used herein, the term "other biological contaminant or pathogen" is intended to mean a contaminant or pathogen other than a biological contaminant or pathogen responsible for TSEs that, upon direct or indirect contact with a biological material, may have a deleterious effect on the biological material or upon a recipient thereof Such other biological contaminants or pathogens include the various viruses, molds, yeasts, bacteria, nanobacteria, mycoplasmas, ureaplasmas and parasites known to those of skill in the art to generally be found in or infect biological materials. Examples of other biological contaminants or pathogens include, but are not limited to, the following: viruses, such as human immunodeficiency viruses and other retroviruses, herpes viruses, filoviruses, circoviruses, paramyxoviruses, cytomegaloviruses, hepatitis viruses (including hepatitis A, B and C and variants thereof), pox viruses, toga viruses, Ebstein-Barr viruses and parvoviruses; bacteria, such as *Escherichia, Bacillus, Campylobacter, Streptococcus* and *Staphalococcus*; nanobacteria; parasites, such as *Trypanosoma* and malarial parasites, including *Plasmodium* species; yeasts; molds; mycoplasmas; and ureaplasmas. As used herein, the term "active biological contaminant or pathogen" is intended to mean a biological contaminant or pathogen that is capable of causing a deleterious effect, either alone or in combination with another factor, such as a second biological contaminant or pathogen or a native protein (wild-type or mutant) or antibody, in the biological material and/or a recipient thereof.

As used herein, the term "blood components" is intended to mean one or more of the components that may be separated from whole blood and include, but are not limited to, the following: cellular blood components, such as red blood cells, white blood cells and platelets; blood proteins, such as blood clotting factors, enzymes, albumin, plasminogen, fibrinogen and immunoglobulins; and liquid blood components, such as plasma, plasma protein fraction (PPF), cryoprecipitate, plasma fractions and plasma-containing compositions.

As used herein, the term "cellular blood component" is intended to mean one or more of the components of whole blood that comprises cells, such as red blood cells, white blood cells, stem cells and platelets.

As used herein, the term "blood protein" is intended to mean one or more of the proteins that are normally found in whole blood. Illustrative examples of blood proteins found in mammals, including humans, include, but are not limited to, the following: coagulation proteins, both vitamin K-dependent, such as Factor VII and Factor IX, and non-vitamin K-dependent, such as Factor VIII and von Willebrands factor; albumin; lipoproteins, including high density lipoproteins and low density lipoproteins; complement proteins; globulins, such as immunoglobulins IgA, IgM, IgG and IgE; and the like. A preferred group of blood proteins includes Factor I (fibrinogen), Factor II (prothrombin), Factor III (tissue factor), Factor V (proaccelerin), Factor VI (accelerin), Factor VII (proconvertin, serum prothrombin conversion), Factor VIII (antihemophiliac factor A), Factor IX (antihemophiliac factor B), Factor X (Stuart-Prower factor), Factor XI (plasma thromboplastin antecedent), Factor XII (Hageman factor), Factor XIII (protransglutamidase), von Willebrands factor (vWF), Factor Ia, Factor IIa, Factor IIIa, Factor Va, Factor VIa, Factor VIIa, Factor VIIIa, Factor IXa, Factor Xa, Factor XIa, Factor XIIa and Factor XIIIa. Another preferred group of blood proteins includes proteins found inside red blood cells, such as hemoglobin and various growth factors, and derivatives of these proteins.

As used herein, the term "liquid blood component" is intended to mean one or more of the fluid, non-cellular components of whole blood, such as plasma (the fluid, non-cellular portion of the whole blood of humans or animals as found prior to coagulation) and serum (the fluid, non-cellular portion of the whole blood of humans or animals as found after coagulation).

As used herein, the term "a biologically compatible solution" is intended to mean a solution to which a biological material may be exposed, such as by being suspended or dissolved therein, and remain viable, i.e., retain its essential biological and physiological characteristics.

As used herein, the term "a biologically compatible buffered solution" is intended to mean a biologically compatible solution having a pH and osmotic properties (e.g., tonicity, osmolality and/or oncotic pressure) suitable for maintaining the integrity of the material(s) therein. Suitable biologically compatible buffered solutions typically have a pH between 4 and 8.5 and are isotonic or only moderately hypotonic or hypertonic. Biologically compatible buffered solutions are known and readily available to those of skill in the art.

As used herein, the term "stabilizer" is intended to mean a compound or material that reduces damage to the biological material being irradiated to a level that is insufficient to preclude the safe and effective use of the material. Illustrative examples of stabilizers include, but are not limited to, the following: antioxidants; free radical scavengers, including spin traps; combination stabilizers, i.e. stabilizers which are effective at quenching both Type I and Type II photodynamic reactions; and ligands, such as heparin, that stabilize the molecules to which they bind. Preferred examples of stabilizers include, but are not limited to, the following: fatty acids, including 6,8-dimercapto-octanoic acid (lipoic acid) and its derivatives and analogues (alpha, beta, dihydro, bisno and tetranor lipoic acid), thioctic acid, 6,8-dimercapto-octanoic acid, dihydrolopoate (DL-6,8-dithioloctanoic acid methyl ester), lipoamide, bisonor methyl ester and tatranor-dihydrolipoic acid, furan fatty acids, oleic and linoleic and palmitic acids and their salts and derivatives; flavonoids, phenylpropaniods, and flavenols, such as quercetin, rutin and its derivatives, apigenin, aminoflavone, catechin, hesperidin and, naringin; carotenes, including beta-carotene; Co-Q10; xanthophylls; polyhydric alcohols, such as glycerol, mannitol; sugars, such as xylose, glucose, ribose, mannose, fructose and trehalose; amino acids and derivatives thereof, such as histidine, N-acetylcysteine (NAC), glutamic acid, tryptophan, sodium capryl N-acetyl tryptophan and methionine; azides, such as sodium azide; enzymes, such as Superoxide Dismutase (SOD) and Catalase; uric acid and its derivatives, such as 1,3-dimethyluric acid and dimethylthiourea; allopurinol; thiols, such as glutathione and reduced glutathione and cysteine; trace elements, such as selenium; vitamins, such as vitamin A, vitamin C (including its derivatives and salts such as sodium ascorbate and palmitoyl ascorbic acid) and vitamin E (and its derivatives and salts such as tocopherol acetate and alpha-tocotrienol); chromanol-alpha-C6; 6-hydroxy-2,5,7,8-tetramethylchroma-2 carboxylic acid (Trolox) and derivatives; extraneous proteins, such as gelatin and albumin; tris-3-methyl-1-phenyl-2-pyrazolin-5-one (MCI-186); citiolone; puercetin; chrysin; dimethyl sulfoxide (DMSO); piperazine diethanesulfonic acid (PIPES); imidazole; methoxypsoralen (MOPS); 1,2-dithiane-4,5-diol; reducing substances, such as butylated hydroxyanisole (BHA) and butylated hydroxytoluene (BHT); cholesterol; probucol; indole derivatives; thimerosal; lazaroid and tirilazad mesylate; proanthenols; proanthocyanidins; ammonium sulfate; Pegorgotein (PEG-SOD); N-tert-butyl-alpha-phenylnitrone (PBN); 4-hydroxy-2,2,6,6-tetramethylpiperidin-1-oxyl (Tempol); mixtures of ascorbate, urate and Trolox C (Asc/urate/Trolox C); proteins and peptides, such as glycylglycine and carnosine, in which each amino acid may be in its D or L form; diosmin; pupurogalin; gallic acid and its derivatives including but not limited to propyl gallate, sodium formaldehyde sulfoxylate and silymarin. Particularly preferred examples include single stabilizers or combinations of stabilizers that are effective at quenching both Type I and Type II photodynamic reactions and volatile stabilizers, which can be applied as a gas and/or easily removed by evaporation, low pressure and similar methods.

As used herein, the term "residual solvent content" is intended to mean the amount or proportion of freely-available liquid in the biological material. Freely-available liquid means the liquid, such as water or an organic solvent (e.g. ethanol, isopropanol, polyethylene glycol, etc.), present in the biological material being sterilized that is not bound to or complexed with one or more of the non-liquid components of the biological material. Freely-available liquid includes intracellular water. The residual solvent contents related as water referenced herein refer to levels determined by the FDA approved, modified Karl Fischer method (Meyer and Boyd, *Analytical Chem.*, 31:215–219, 1959; May, et al., *J. Biol. Standardization*, 10:249–259, 1982; Centers for Biologics Evaluation and Research, FDA, Docket No. 89D-0140, 83–93; 1990) or by near infrared spectroscopy. Quantitation of the residual levels of other solvents may be determined by means well known in the art, depending upon which solvent is employed. The proportion of residual solvent to solute may also be considered to be a reflection of the concentration of the solute within the solvent. When so expressed, the greater the concentration of the solute, the lower the amount of residual solvent.

As used herein, the term "sensitizer" is intended to mean a substance that selectively targets viral, bacterial, prion and/or parasitic contaminants, rendering them more sensitive to inactivation by radiation, therefore permitting the use of a lower rate or dose of radiation and/or a shorter time of irradiation than in the absence of the sensitizer. Illustrative examples of suitable sensitizers include, but are not limited to, the following: psoralen and its derivatives and analogs (including 3-carboethoxy psoralens); inactines and their derivatives and analogs; angelicins, khellins and coumarins which contain a halogen substituent and a water solubilization moiety, such as quaternary ammonium ion or phosphonium ion; nucleic acid binding compounds; brominated hematoporphyrin; phthalocyanines; purpurins; porphorins; halogenated or metal atom-substituted derivatives of dihematoporphyrin esters, hematoporphyrin derivatives, benzoporphyrin derivatives, hydrodibenzoporphyrin dimaleimade, hydrodibenzoporphyrin, dicyano disulfone, tetracarbethoxy hydrodibenzoporphyrin, and tetracarbethoxy hydrodibenzoporphyrin dipropionamide; doxorubicin and daunomycin, which may be modified with halogens or metal atoms; netropsin; BD peptide, S2 peptide; S-303 (ALE compound); dyes, such as hypericin, methylene blue, eosin, fluoresceins (and their derivatives), flavins, merocyanine 540; photoactive compounds, such as bergapten; and SE peptide. In addition, atoms which bind to prions, and thereby increase their sensitivity to inactivation by radiation, may also be use. An illustrative example of such an atom would be the Copper ion, which binds to the prior protein and, with a Z number higher than the other atoms in the protein, increases the probability that the prion protein will absorb energy during irradiation, particularly gamma irradiation.

As used herein, the term "proteinaceous material" is intended to mean any material derived or obtained from a living organism that comprises at least one protein or peptide. A proteinaceous material may be a naturally occurring material, either in its native state or following processing/purification and/or derivatization, or an artificially produced material, produced by chemical synthesis or recombinant/transgenic technology and, optionally, process/purified and/or derivatized. Illustrative examples of proteinaceous materials include, but are not limited to, the following: proteins and peptides produced from cell culture; milk and other dairy products; ascites; hormones; growth factors; materials, including pharmaceuticals, extracted or isolated from animal tissue, such as heparin and insulin, or plant matter; plasma, including fresh, frozen and freeze-dried, and plasma protein fraction; fibrinogen and derivatives thereof, fibrin, fibrin I, fibrin II, soluble fibrin and fibrin monomer, and/or fibrin sealant products; whole blood; protein C; protein S; alpha-1 anti-trypsin (alpha-1 protease inhibitor); butyl-cholinesterase; anticoagulants, such as coumarin drugs (warfarin); streptokinase; tissue plasminogen activator (tPA); erythropoietin (EPO); urokinase; neupogen; anti-thrombin-3; alpha-glucosidase; (fetal) bovine serum/horse serum; meat; immunoglobulins, including anti-sera, monoclonal antibodies, polyclonal antibodies and genetically engineered or produced antibodies; albumin; alpha-globulins; beta-globulins; gamma-globulins; coagulation proteins; complement proteins; and interferons.

As used herein, the term "radiation" is intended to mean radiation of sufficient energy to sterilize at least some component of the irradiated biological material. Types of radiation include, but are not limited to, the following: (i) corpuscular (streams of subatomic particles such as neutrons, electrons, and/or protons); (ii) electromagnetic (originating in a varying electromagnetic field, such as radio waves, visible (both mono and polychromatic) and invisible light, infrared, ultraviolet radiation, x-radiation, and gamma rays and mixtures thereof); and (iii) sound and pressure waves. Such radiation is often described as either ionizing (capable of producing ions in irradiated materials) radiation, such as gamma rays, and non-ionizing radiation, such as visible light. The sources of such radiation may vary and, in general, the selection of a specific source of radiation is not critical provided that sufficient radiation is given in an appropriate time and at an appropriate rate to effect sterilization. In practice, gamma radiation is usually produced by isotopes of Cobalt or Cesium, while UV and X-rays are produced by machines that emit UV and X-radiation, respectively, and electrons are often used to sterilize materials in a method known as "e-beam" irradiation that involves their production via a machine. Visible light, both mono- and polychromatic, is produced by machines and may, in practice, be combined with invisible light, such as infrared and UV, that is produced by the same machine or a different machine.

As used herein, the term "to protect" is intended to mean to reduce any damage to the biological material being irradiated, that would otherwise result from the irradiation of that material, to a level that is insufficient to preclude the safe and effective use of the material following irradiation. In other words, a substance or process "protects" a biological material from radiation if the presence of that substance or carrying out that process results in less damage to the material from irradiation than in the absence of that substance or process. Thus, biological material may be used safely and effectively after irradiation in the presence of a substance or following performance of a process that "protects" the material, but could not be used safely and effectively after irradiation under identical conditions but in the absence of that substance or the performance of that process.

B. Particularly Preferred Embodiments

A first preferred embodiment of the present invention is directed to a method for sterilizing a biological material that is sensitive to radiation comprising irradiating the biological material with radiation for a time effective to sterilize the material at a rate effective to sterilize the material and to protect the material from radiation.

Another preferred embodiment of the present invention is directed to a method for sterilizing a biological material that is sensitive to radiation comprising: (i) adding to a biological material at least one stabilizer in an amount effective to protect the biological material from radiation; and (ii) irradiating the biological material with radiation at an effective rate for a time effective to sterilize the material.

Another preferred embodiment of the present invention is directed to a method for sterilizing a biological material that is sensitive to radiation comprising: (i) reducing the residual solvent content of a biological material to a level effective to protect the biological material from radiation; and (ii) irradiating the biological material with radiation at an effective rate for a time effective to sterilize the biological material.

Another preferred embodiment of the present invention is directed to a method for sterilizing a biological material that is sensitive to radiation comprising: (i) reducing the temperature of a biological material to a level effective to protect the biological material from radiation; and (ii) irradiating the biological material with radiation at an effective rate for a time effective to sterilize the biological material.

Another preferred embodiment of the present invention is directed to a method for sterilizing a biological material that is sensitive to radiation comprising: (i) applying to the biological material a stabilizing process selected from the group consisting of: (a) reducing the residual solvent content of a biological material, (b) adding to the biological material at least one stabilizer, and (c) reducing the temperature of the biological material; and (ii) irradiating the biological material with radiation at an effective rate for a time effective to sterilize the biological material, wherein the stabilizing process and the rate of irradiation are together effective to protect the biological material from radiation.

Another preferred embodiment of the present invention is directed to a method for sterilizing a biological material that is sensitive to radiation comprising: (i) applying to the biological material at least two stabilizing processes selected from the group consisting of: (a) reducing the residual solvent content of a biological material, (b) adding to the biological material at least one stabilizer, and (c) reducing the temperature of the biological material; and (ii) irradiating the biological material with radiation at an effective rate for a time effective to sterilize the biological material, wherein the stabilizing processes may be performed in any order and are together effective to protect the biological material from radiation.

According to the methods of the present invention, a stabilizer is added prior to irradiation of the biological material with radiation. This stabilizer is preferably added to the biological material in an amount that is effective to protect the biological material from the radiation. Suitable amounts of stabilizer may vary depending upon certain features of the particular method(s) of the present invention being employed, such as the particular stabilizer being used and/or the nature and characteristics of the particular biological material being irradiated and/or its intended use, and can be determined empirically by one skilled in the art.

According to certain methods of the present invention, the residual solvent content of the biological material is reduced prior to irradiation of the biological material with radiation. The residual solvent content is preferably reduced to a level that is effective to protect the biological material from the radiation. Suitable levels of residual solvent content may vary depending upon certain features of the particular method(s) of the present invention being employed, such as the nature and characteristics of the particular biological material being irradiated and/or its intended use, and can be determined empirically by one skilled in the art. There may be biological materials for which it is desirable to maintain the residual solvent content to within a particular range, rather than a specific value.

When the solvent is water, and particularly when the biological material is in a solid phase, the residual solvent content is generally less than about 15%, typically less than about 10%, usually less than about 5%, preferably less than about 3.0%, more preferably less than about 2.0%, even more preferably less than about 1.0%, still more preferably less than about 0.5%, still even more preferably less than about 0.2% and most preferably less than about 0.08%.

The solvent may preferably be a non-aqueous solvent, more preferably a non-aqueous solvent that is not prone to the formation of free-radicals upon irradiation, and most preferably a non-aqueous solvent that is not prone to the formation of free-radicals upon irradiation and that has little or no dissolved oxygen or other gas(es) that is (are) prone to the formation of free-radicals upon irradiation. Volatile solvents are particularly preferred.

In a preferred embodiment, when the residual solvent is water, the residual solvent content of a biological material is reduced by dissolving or suspending the biological material in a non-aqueous solvent that is capable of dissolving water. Preferably, such a non-aqueous solvent is not prone to the formation of free-radicals upon irradiation and has little or no dissolved oxygen or other gas(es) that is (are) prone to the formation of free-radicals upon irradiation.

When the biological material is in a liquid phase, reducing the residual solvent content may be accomplished by any of a number of means, such as by increasing the solute concentration. In this manner, the concentration of the biological material dissolved within the solvent may be increased to generally at least about 0.5%, typically at least about 1%, usually at least about 5%, preferably at least about 10%, more preferably at least about 15%, even more preferably at least about 20%, still even more preferably at least about 25%, and most preferably at least about 50%.

In certain embodiments of the present invention, the residual solvent content of a particular biological material may be found to lie within a range, rather than at a specific point. Such a range for the preferred residual solvent content of a particular biological material may be determined empirically by one skilled in the art.

While not wishing to be bound by any theory of operability, it is believed that the reduction in residual solvent content reduces the degrees of freedom of the biological material, reduces the number of targets for free radical generation and may restrict the solubility of these free radicals. Similar results might therefore be achieved by lowering the temperature of the biological material below its eutectic point or below its freezing point, or by vitrification to likewise reduce the degrees of freedom of the biological material. These results may permit the use of a higher rate and/or dose of radiation than might otherwise be acceptable. Thus, the methods described herein may be performed at any temperature that doesn't result in unacceptable damage to the biological material, i.e., damage that would preclude the safe and effective use of the biological material. Preferably, the methods described herein are performed at ambient temperature or below ambient temperature, such as below the eutectic point or freezing point of the biological material being irradiated.

In accordance with the methods of the present invention, an "acceptable level" of damage may vary depending upon certain features of the particular method(s) of the present invention being employed, such as the nature and characteristics of the particular biological material and/or dipeptide stabilizer being used, and/or the intended use of the biological material being irradiated, and can be determined empirically by one skilled in the art. An "unacceptable level" of damage would therefore be a level of damage that would preclude the safe and effective use of the biological material being sterilized. The particular level of damage in a given biological material may be determined using any of the methods and techniques known to one skilled in the art.

The residual solvent content of the biological material may be reduced by any of the methods and techniques known to those skilled in the art for reducing solvent from a biological material without producing an unacceptable level of damage to the biological material. Such methods include, but are not limited to, evaporation, concentration, centrifugal concentration, vitrification and spray-drying.

A particularly preferred method for reducing the residual solvent content of a biological material is lyophilization.

Another particularly preferred method for reducing the residual solvent content of a biological material is vitrification, which may be accomplished by any of the methods and techniques known to those skilled in the art, including the addition of solute and or additional solutes, such as sucrose, to raise the eutectic point of the biological material, followed by a gradual application of reduced pressure to the biological material in order to remove the residual solvent, such as water. The resulting glassy material will then have a reduced residual solvent content.

According to certain methods of the present invention, the biological material to be sterilized may be immobilized upon a solid surface by any means known and available to one skilled in the art. For example, the biological material to be sterilized may be present as a coating or surface on a biological or non-biological substrate.

The radiation employed in the methods of the present invention may be any radiation effective for the sterilization of the biological material being treated. The radiation may be corpuscular, including e-beam radiation. Preferably the radiation is electromagnetic radiation, including x-rays, infrared, visible light, UV light and mixtures of various wavelengths of electromagnetic radiation. A particularly preferred form of radiation is gamma radiation.

According to the methods of the present invention, the biological material is irradiated with the radiation at a rate effective for the sterilization of the biological material, while not producing an unacceptable level of damage to that material. Suitable rates of irradiation may vary depending upon certain features of the methods of the present invention being employed, such as the nature and characteristics of the particular biological material being irradiated, the particular form of radiation involved and/or the particular biological contaminants or pathogens being inactivated. Suitable rates of irradiation can be determined empirically by one skilled in the art. Preferably, the rate of irradiation is constant for the duration of the sterilization procedure. When this is impractical or otherwise not desired, a variable or discontinuous irradiation may be utilized.

According to the methods of the present invention, the rate of irradiation may be optimized to produce the most advantageous combination of product recovery and time required to complete the operation. Both low ($\leq 3$ kGy/hour) and high (>3 kGy/hour) rates may be utilized in the methods described herein to achieve such results. The rate of irradiation is preferably be selected to optimize the recovery of the biological material while still sterilizing the biological material. Although reducing the rate of irradiation may serve to decrease damage to the biological material, it will also result in longer irradiation times being required to achieve a particular desired total dose. A higher dose rate may therefore be preferred in certain circumstances, such as to minimize logistical issues and costs, and may be possible when used in accordance with the methods described herein for protecting a biological material from irradiation.

According to a particularly preferred embodiment of the present invention, the rate of irradiation is not more than about 3.0 kGy/hour, more preferably between about 0.1 kGy/hr and 3.0 kGy/hr, even more preferably between about 0.25 kGy/hr and 2.0 kGy/hour, still even more preferably between about 0.5 kGy/hr and 1.5 kGy/hr and most preferably between about 0.5 kGy/hr and 1.0 kGy/hr.

According to another particularly preferred embodiment of the present invention, the rate of irradiation is at least about 3.0 kGy/hr, more preferably at least about 6 kGy/hr, even more preferably at least about 16 kGy/hr, and even more preferably at least about 30 kGy/hr and most preferably at least about 45 kGy/hr or greater.

According to the methods of the present invention, the biological material to be sterilized is irradiated with the radiation for a time effective for the sterilization of the biological material. Combined with irradiation rate, the appropriate irradiation time results in the appropriate dose of irradiation being applied to the biological material. Suitable irradiation times may vary depending upon the particular form and rate of radiation involved and/or the nature and characteristics of the particular biological material being irradiated. Suitable irradiation times can be determined empirically by one skilled in the art.

According to the methods of the present invention, the biological material to be sterilized is irradiated with radiation up to a total dose effective for the sterilization of the biological material, while not producing an unacceptable level of damage to that material. Suitable total doses of radiation may vary depending upon certain features of the methods of the present invention being employed, such as the nature and characteristics of the particular biological material being irradiated, the particular form of radiation involved and/or the particular biological contaminants or pathogens being inactivated. Suitable total doses of radiation can be determined empirically by one skilled in the art. Preferably, the total dose of radiation is at least 25 kGy, more preferably at least 45 kGy, even more preferably at least 75 kGy, and still more preferably at least 100 kGy or greater, such as 150 kGy or 200 kGy.

The particular geometry of the biological material being irradiated, such as the thickness and distance from the source of radiation, may be determined empirically by one skilled in the art.

According to certain methods of the present invention, an effective amount of at least one sensitizing compound may optionally be added to the biological material prior to irradiation, for example to enhance the effect of the irradiation on the biological contaminant(s) or pathogen(s) therein, while employing the methods described herein to minimize the deleterious effects of irradiation upon the biological material. Suitable sensitizers are known to those skilled in the art, and include psoralens and their derivatives and inactines and their derivatives.

According to the methods of the present invention, the irradiation of the biological material may occur at any temperature which is not deleterious to the biological material being sterilized. According to one preferred embodiment, the biological material is irradiated at ambient temperature. According to an alternate preferred embodiment, the biological material is irradiated at reduced temperature, i.e. a temperature below ambient temperature, such as 0° C., −40° C., −78° C. or −196° C. According to this embodiment of the present invention, the biological material is preferably irradiated at or below the freezing or eutectic point of the biological material. According to another alternate preferred embodiment, the biological material is irradiated at elevated temperature, i.e. a temperature above ambient temperature, such as 37° C., 60° C., 72° C. or 80° C. While not wishing to be bound by any theory, the use of elevated temperature may enhance the effect of irradiation on the biological contaminant(s) or pathogen(s) and therefore allow the use of a lower total dose of radiation.

According to the methods of the present invention, the irradiation of the biological material may occur at any pressure which is not deleterious to the biological material being sterilized. According to one preferred embodiment, the biological material is irradiated at elevated pressure. More preferably, the biological material is irradiated at elevated pressure due to the application of sound waves or the use of a volatile. While not wishing to be bound by any theory, the use of elevated pressure may enhance the effect of irradiation on the biological contaminant(s) or pathogen(s) and therefore allow the use of a lower total dose of radiation.

Generally, according to the methods of the present invention, the pH of the biological material undergoing sterilization is about 7. In some embodiments of the present invention, however, in order to avoid aggregation of the components of the biological material (such as in the case of immunoglobulins) or for other reasons, the biological material may have a pH of less than 7, preferably less than or equal to 6, more preferably less than or equal to 5, even more preferably less than or equal to 4, and most preferably less than or equal to 3. In alternative embodiments of the present invention, the biological material may have a pH of greater than 7, preferably greater than or equal to 8, more preferably greater than or equal to 9, even more preferably greater than or equal to 10, and most preferably greater than or equal to 11.

Similarly, according to the methods of the present invention, the irradiation of the biological material may occur under any atmosphere that is not deleterious to the biological material being treated. According to one preferred embodiment, the biological material is held in a low oxygen atmosphere or an inert atmosphere. When an inert atmosphere is employed, the atmosphere is preferably composed of a noble gas, such as helium or argon, more preferably a higher molecular weight noble gas, and most preferably argon. According to another preferred embodiment, the biological material is held under vacuum while being irradiated. According to a particularly preferred embodiment of the present invention, a biological material (lyophilized, liquid or frozen) is stored under vacuum or an inert atmosphere (preferably a noble gas, such as helium or argon, more preferably a higher molecular weight noble gas, and most preferably argon) prior to irradiation. According to an alternative preferred embodiment of the present invention, a liquid preparation of a biological material is held under low pressure, to decrease the amount of gas dissolved in the liquid, prior to irradiation, either with or without a prior step of solvent reduction, such as lyophilization.

In another preferred embodiment, where the biological material contains oxygen or other gases dissolved within or associated with it, the amount of these gases within or associated with the biological material may be reduced by any of the methods and techniques known and available to those skilled in the art, such as the controlled reduction of pressure within a container (rigid or flexible) holding the biological material to be treated or by placing the biological material in a container of approximately equal volume.

In certain embodiments of the present invention, when the biological material to be treated is a tissue, at least one stabilizer is introduced according to any of the methods and techniques known and available to one skilled in the art, including soaking the tissue in a solution containing the stabilizer(s), preferably under pressure, at elevated temperature and/or in the presence of a penetration enhancer, such as dimethylsulfoxide. Other methods of introducing at least one stabilizer into a tissue include, but are not limited to, applying a gas containing the stabilizer(s), preferably under pressure and/or at elevated temperature, injection of the stabilizer(s) or a solution containing the stabilizer(s) directly into the tissue, placing the tissue under reduced pressure and then introducing a gas or solution containing the stabilizer(s) and combinations of two or more of these methods. One or more sensitizers may also be introduced into a tissue according to such methods.

In certain particularly preferred embodiments of the present invention, the sterilization of the biological material will also result in a reduction in the level of at least one other biological contaminant or pathogen, such as a virus, present in the material.

It will be appreciated that the combination of one or more of the features described herein may be employed to further minimize undesirable effects upon the biological material caused by irradiation, while maintaining adequate effectiveness of the irradiation process on the biological contaminant(s) or pathogen(s). For example, in addition to the use of a stabilizer, a particular biological material may also be lyophilized and kept under vacuum prior to irradiation to further minimize undesirable effects.

The sensitivity of a particular biological contaminant or pathogen to radiation is commonly calculated by determining the dose necessary to inactivate or kill all but 37% of the agent in a sample, which is known as the $D_{37}$ value. In accordance with certain preferred methods of the present invention, the sterilization of a biological material results in a decrease in the $D_{37}$ value of the biological contaminant or pathogen without a concomitant decrease in the $D_{37}$ value of the biological material. In accordance with other preferred methods of the present invention, the sterilization of a biological material results in an increase in the $D_{37}$ value of the biological material. In accordance with the most preferred methods of the present invention, the sterilization of a biological material results in a decrease in the $D_{37}$ value of the biological contaminant or pathogen and a concomitant increase in the $D_{37}$ value of the biological material.

EXAMPLES

The following examples are illustrative, but not limiting, of the present invention. Other suitable modifications and adaptations are of the variety normally encountered by those skilled in the art and are fully within the spirit and scope of the present invention. Unless otherwise noted, all irradiation was accomplished using a $^{60}$Co source.

Example 1

Human albumin (25%) was spiked 1:100 with 10% brain homogenate from hamster adapted scrapie (strain 263K). The sample was mixed by vortexing, and 4 6-ml aliquots of scrapie-spiked albumin were dispensed into 10-ml serum vials. One vial was stored at −80° C. as a frozen control. Three vials were taken to a commercial irradiation facility. One vial (the 0 kGy control) was refrigerated to prevent bacterial growth. The remaining vials were irradiated at ambient temperature (20–25° C.) at a rate of 0.4 kGy/hr to a total dose of 26 or 50 kGy. Radiation dose was assessed by dosimeters attached to each vial and by external dosimeters placed in close proximity to the vials. The irradiated samples and the 0 kGy control were assayed for scrapie infectivity.

Infectivity was assayed by intracerebral inoculation of 0.05 ml of sample into 12 hamsters, which were then held for up to 6 months for observation. Three clinical endpoints were assessed: wobble, failure-to-rear and death. There was an at least 8–10 day delay in the appearance of each clinical symptom in the group inoculated with the sample treated at the higher dose compared with the unirradiated control. The data were compared with a nomogram constructed from the dose response of the incubation time for a large number of animals infected in limiting dilution series mode (R. Rowher, unpublished data). This nomogram correlated days to onset of disease (as evidenced by wobble) with $\log_{10}$ $LD_{50}$ inoculated.

The effect of the radiation on the biological material (albumin) was determined by SDS-PAGE gel electrophoresis and high performance size exclusion chromatography as follows.

SDS-PAGE was conducted in 8% polyacrylamide gels in a Mighty Small Mini-Vertical Unit SE250/SE260. Samples were diluted 1:100 in PBS and then 1:1 in Laemmli Sample Buffer (Bio-Rad) with or without 5% β-mercaptoethanol. Sample load was 12.5 µg per lane. The molecular weight markers were Low-Range Standard (Bio-Rad). Electrophoresis was conducted for 30 minutes at 125 volts. Gels were stained with 0.1% Coomassie Brilliant Blue R-250 in 50% methanol, 10% acetic acid and destained with 5% methanol, 9% acetic acid.

HPSEC was performed on 7.8×300 mm Biosep SEC columns (Phenomenex, Torrence, Calif.) in 130A Separation System (Applied Biosystems). The eluant buffer of 0.05M sodium phosphate, 0.1 M sodium chloride (pH 6.7) was filtered before use with 0.22 µm filters. Albumin solutions were diluted to a final concentration of 1.25 mg/ml in eluant buffer and 25 µl (31.25 µg protein) was injected. Flow rate was 1 ml/min. Detection was by absorbance at 280 nm.

Results

For the unirradiated control, the median incubation time for onset of disease (wobble) was 75 days. For the irradiated samples, the median incubation time for onset of disease was 88 days for the sample irradiated to a total dose of 25 kGy and 90 days for the sample irradiated to 50 kGy. Comparison with the nomogram gave estimated values for the $\log_{10}$ titers as 6.5 for the unirradiated control and 4.8 and 4.6 for the samples irradiated to 25 kGy and 50 kGy, respectively. Based on these estimates, the median reduction factors for the irradiated samples were 1.7 and 1.9 for the samples irradiated to 25 kGy and 50 kGy, respectively These represent estimates of the median reduction values, but do not convey the maximum possible reduction predicted by this experiment. To do this, the minimum value of the 95% confidence interval (CI) of the control group should be compared with the maximum value of the 95% CI of the radiation treated groups. This calculation will yield the maximum reduction factor of the titres that lies within the 95% CI. For the 50 kGy group this value was 3.5 logs reduction.

The susceptibility of biological contaminants or pathogens to radiation is often expressed as their $D_{37}$ value. This represents the dose of radiation required to reduce the number of active biological contaminants or pathogens to 37% of their pre-irradiation number. Thus the lower the $D_{37}$, the more susceptible a particular biological contaminant or pathogen is to the effects of the radiation. The $D_{37}$ of the scrapie prion has been determined experimentally to be approximately 47 kGy (Rohwer, Nature, 308, 5960, pp. 658–662, 1984). Utilizing the methodology described herein, the $D_{37}$ of the scrapie prion was unexpectedly found to be only 4.5 kGy. Thus the $D_{37}$ of the prion was decreased using the methods and formulation employed in this experiment. Thus increased destruction of the scrapie prion was achieved while maintaining the integrity of the biological material, a commercial therapeutic 25% solution of human albumin, used in this experiment.

Figure 4A:
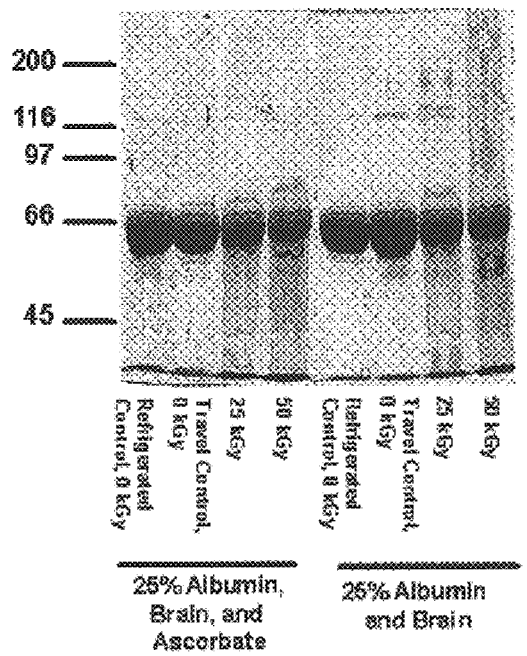
Figure 4B:
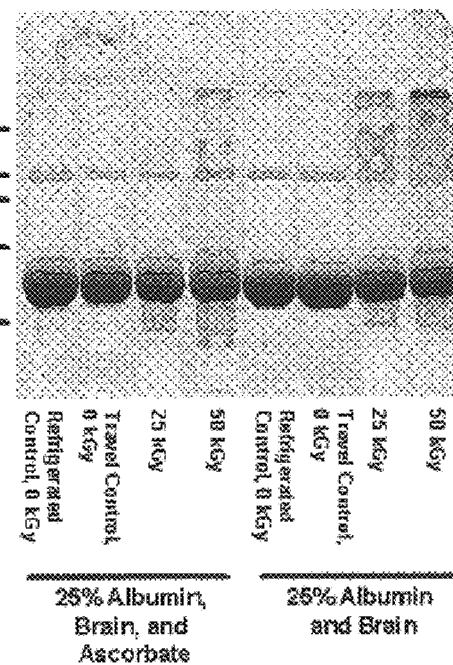
Figure 4C:
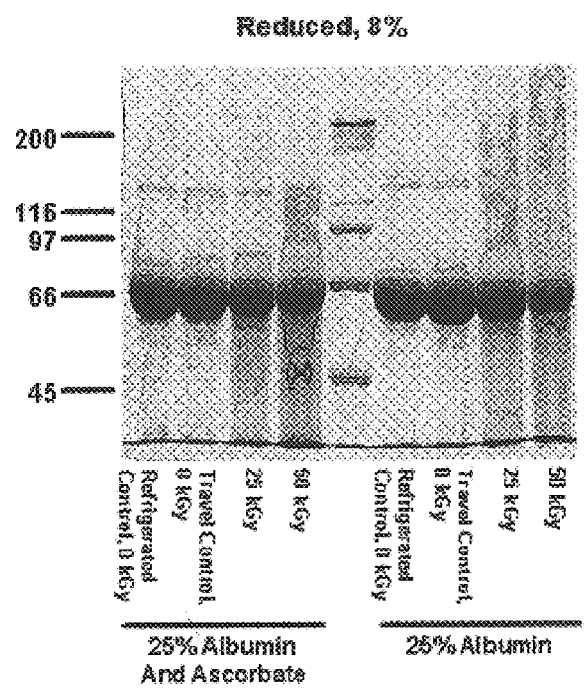
Figure 4D:
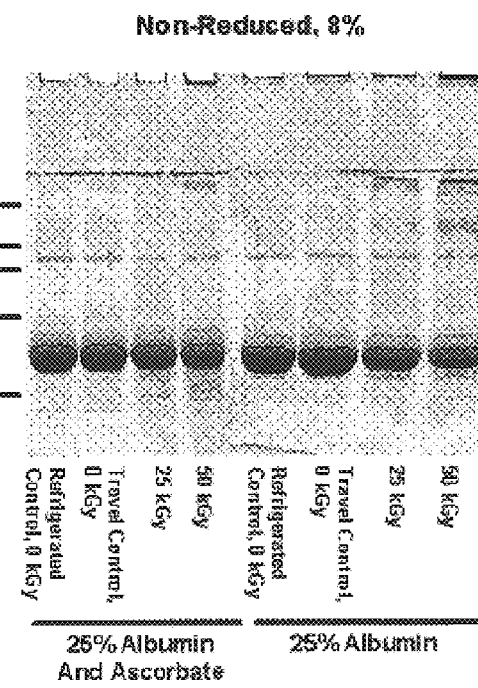
Figure 5A:
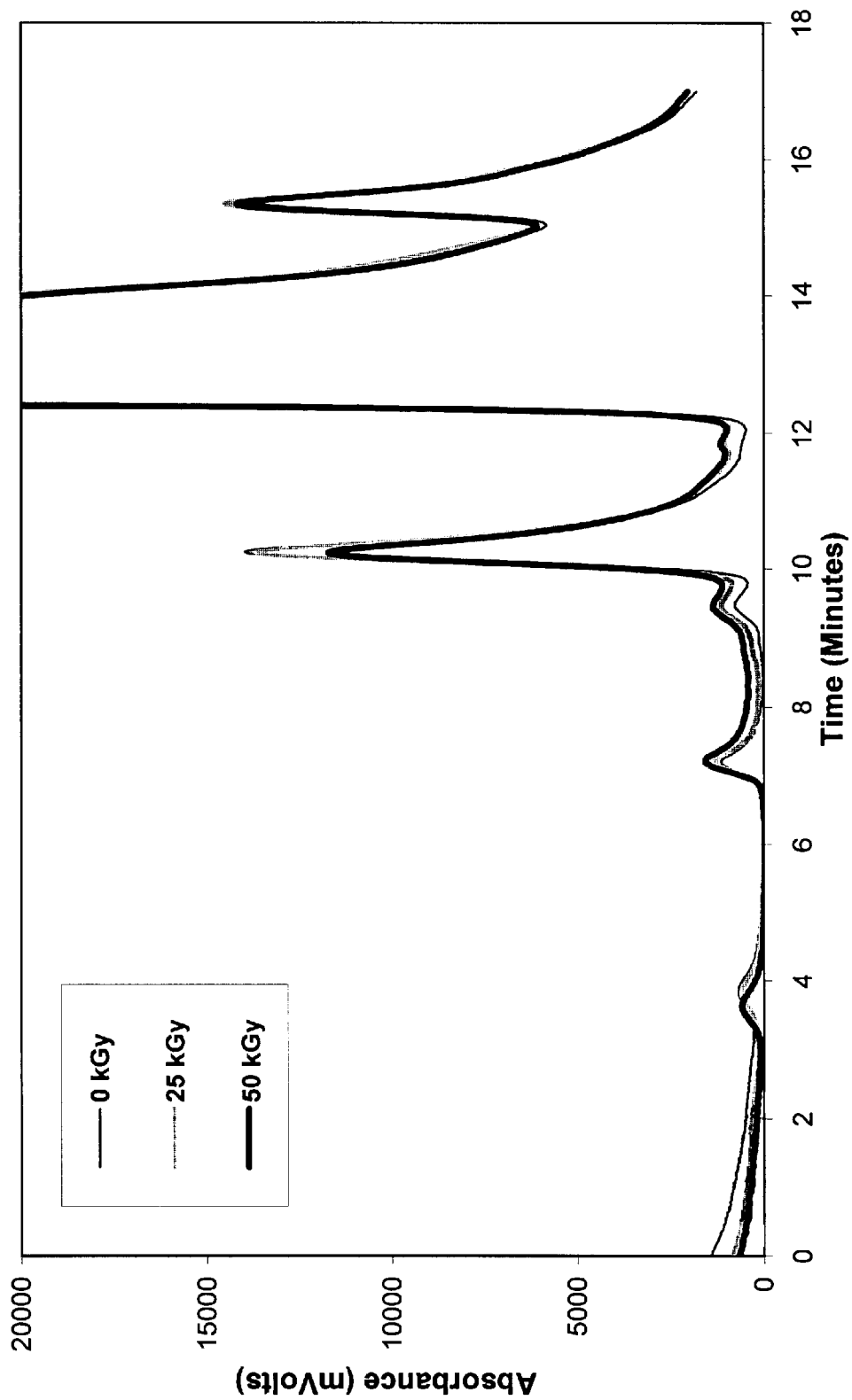
Figure 5C:
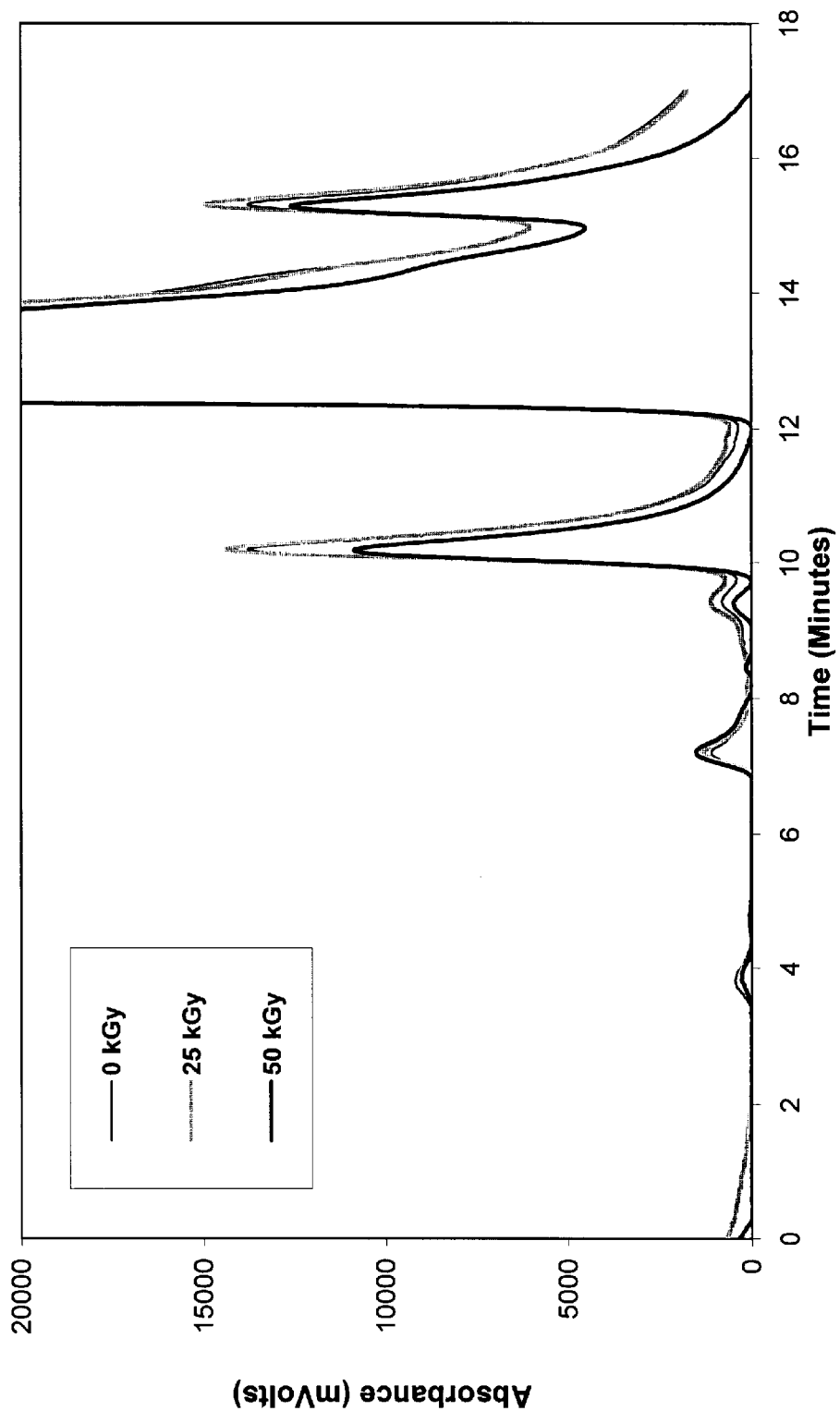
Figure 5D:
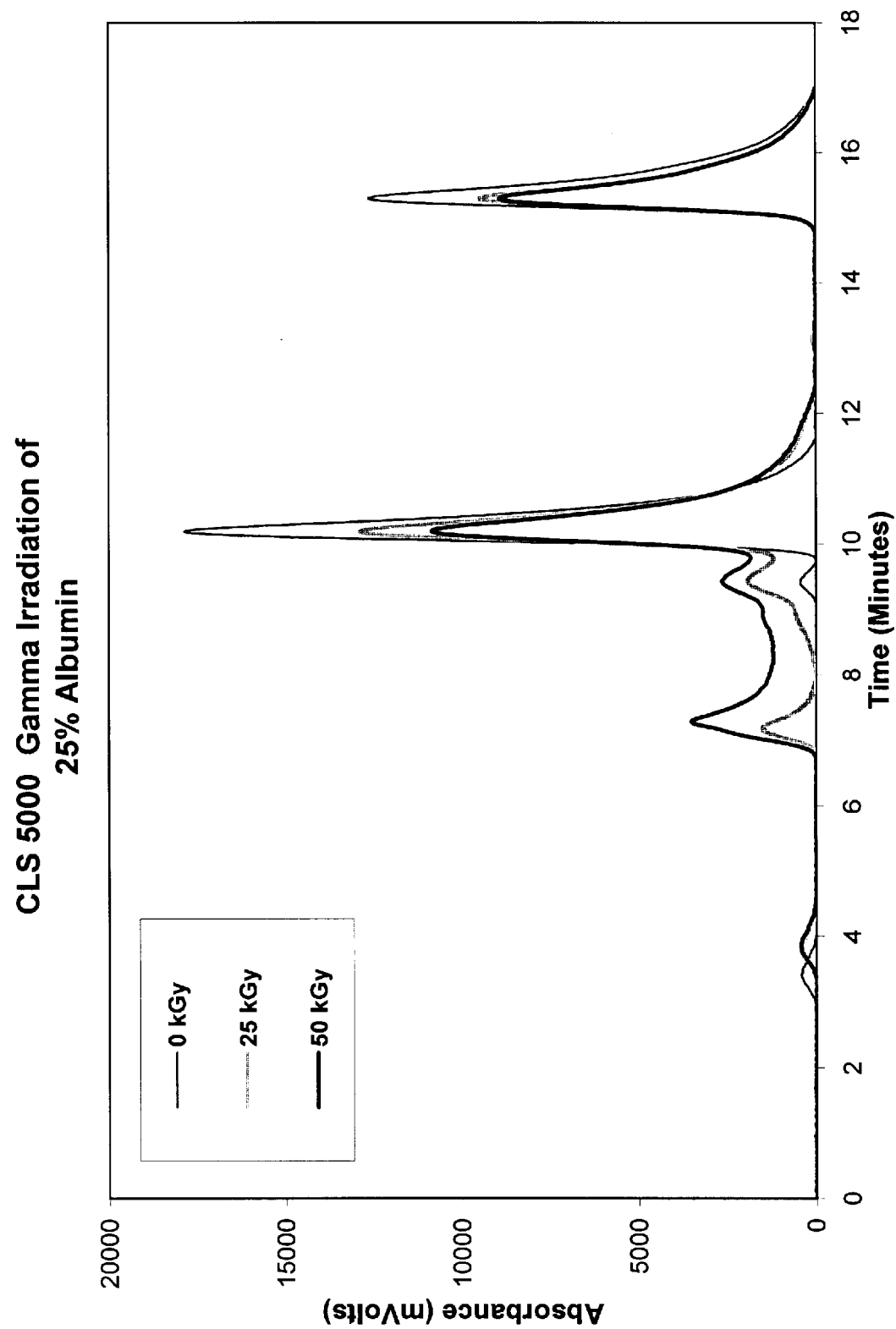

Increased destruction of the scrapie prion was achieved while maintaining the essential biological and physiological characteristics of the biological material being treated. This particular biological material, a 25% solution of human albumin, was examined both pre- and post-irradiation with gamma radiation to total doses of 25, 50 and 100 kGy. As shown by gel electrophoresis (FIGS. 4A–4B), the albumin was largely intact at radiation doses up to 50 kGy, with only a small amount of fragmentation and aggregation and a slight decrease in the amount of the monomeric form of albumin. The results were similar for all of the albumin samples, irrespective of whether they contained any ascorbate and/or hamster. At higher doses, minor changes were seen in the albumin samples, mostly in the form of an increased polymerization of albumin.

A more detailed analysis was made using HPSEC. As shown in FIGS. 5A–5D, with irradiation, the amount of albumin monomer decreased (peak at 10.5 min), the amount of dimer increased (9 min) and the amount of polymer increased (7.2 min). These changes were all minimized in the presence of ascorbate. The remaining peaks at 12.6 and 15.3 min are those of ascorbate and the N-acetyl tryptophan stabilizer, respectively.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. A composition comprising at least one biological material and at least one stabilizer in an amount effective to preserve said biological material for sterilization with radiation, wherein said biological material is glassy or vitrified.

2. The composition according to claim 1, wherein said at least one stabilizer is selected from the group consisting of polyhydric alcohols, DMSO and mixtures thereof.

3. The composition according to claim 2, wherein said polyhydric alcohols are selected from the group consisting of trehalose, mannitol, glycerol and combinations thereof.

4. The composition according to claim 1, wherein said at least one stabilizer comprises trehalose.

5. The composition according to claim 1, wherein said at least one stabilizer comprises a polyhydric alcohol.

6. The composition according to claim 1, wherein said at least one stabilizer comprises glycerol.

7. The composition according to claim 1, wherein said at least one stabilizer comprises mannitol.

8. The composition according to claim 1, wherein said at least one stabilizer comprises DMSO.

9. A composition comprising at least one biological material with residual solvent content, wherein the residual solvent content of said biological material is at a level effective to preserve said biological material for sterilization with radiation, wherein said biological material is glassy or vitrified.

10. The composition of claim 9, wherein said residual solvent content is less than 15%.

11. The composition of claim 9, wherein said residual solvent content is less than 10%.

12. The composition of claim 9, wherein said residual solvent content is less than 5%.

13. The composition of claim 9, wherein said residual solvent content is less than 2%.

14. The composition of claim 9, wherein said residual solvent content is less than 1%.

15. The composition of claim 9, wherein said residual solvent content is less than 0.5%.

16. The composition of claim 9, wherein said residual solvent content is less than 0.08%.

17. The composition of claim 1 or 9, wherein said biological material is selected from the group consisting of monoclonal immunoglobulins, polyclonal immunoglobulins, glycosidases, sulfatases, urokinase and Factor VIII.

18. The composition according to claim 1 or 9, wherein said biological material is selected from the group consisting of cells, tissues, blood, blood components, proteins, enzymes, immunoglobulins, botanicals, food, ligaments, tendons, nerves, bone, demineralized bone matrix, grafts, joints, femurs, femoral heads, teeth, skin grafts, bone marrow, heart valves, cartilage, corneas, arteries, veins, meat, organs, limbs, digits, lipids, carbohydrates, collagen, chitin, stem cells, islet of Langerhans cells, genetically altered cells, red blood cells, white blood cells, proteinaceous material and combinations thereof.

19. The composition according to claim 18, wherein said blood components are selected from the group consisting of cellular blood components, blood proteins, liquid blood components and combinations thereof.

20. The composition according to claim 18, wherein said collagen is selected from the group consisting of native collagen, afibrillar collagen, atelomeric collagen, soluble collagen and insoluble collagen.

21. The composition according to claim 18, wherein said biological material comprises a protein or peptide produced from cell culture.

22. The composition according to claim 1 or 9, wherein said biological material is whole or processed.

23. The composition according to claim 1 or 9, wherein said biological material is selected from the group consisting of hearts, livers, lungs, kidneys, intestines and pancreas.

24. The composition according to claim 1 or 9, wherein said biological material is human.

25. The composition according to claim 1 or 9, wherein said biological material is mammalian.

26. The composition according to claim 1 or 9, wherein said biological material is bovine.

27. The composition according to claim 1 or 9, wherein said biological material is equine.

28. The composition according to claim 1 or 9, wherein said biological material is porcine.

29. The composition according to claim 1 or 9, wherein said biological material is transgenic or recombinant.

30. The composition according to claim 29, wherein said biological material is milk.

31. The composition according to claim 1 or 9, wherein said biological material is milk, collagen, plasma or serum.

32. The composition according to claim 1 or 9, wherein said biological material is selected from the group consisting of ligaments, tendons, nerves, bone, teeth, bone marrow, skin grafts, cartilage, corneas, arteries, veins and organs for transplantation.

33. The composition according to claim 1 or 9, wherein said biological material is tissue.

34. The composition according to claim 33, wherein said tissue is selected from the group consisting of bone, grafts, joints, femurs, femoral heads, heart valves, ligaments, hearts, livers, lungs, kidneys, intestines, pancreas, limbs, digits and demineralized bone matrix.

35. The composition according to claim 1 or 9, wherein said biological material is bovine serum.

36. The composition according to claim 35, wherein said biological material is fetal bovine serum.

37. A method for sterilizing a biological material that is sensitive to radiation, said method comprising
adding to said biological material at least one stabilizer; and
irradiating said biological material with radiation for a time effective to sterilize said biological material at a rate effective to sterilize and protect said biological material from said radiation, wherein said biological material is glassy or vitrified.

38. The method according to claim 37, wherein said at least one stabilizer is selected from the group consisting of polyhydric alcohols, DMSO and mixtures thereof.

39. The method according to claim 38, wherein said polyhydric alcohols are selected from the group consisting of trehalose, mannitol, glycerol and combinations thereof.

40. The method according to claim 37, wherein said at least one stabilizer comprises trehalose.

41. The method according to claim 37, wherein said at least one stabilizer comprises a polyhydric alcohol.

42. The method according to claim 37, wherein said at least one stabilizer comprises glycerol.

43. The method according to claim 37, wherein said at least one stabilizer comprises mannitol.

44. The method according to claim 37, wherein said at least one stabilizer comprises DMSO.

45. A method for sterilizing a biological material comprising residual solvent content, wherein said biological material is sensitive to radiation, said method comprising
reducing the residual solvent content of said biological material; and
irradiating said biological material with radiation for a time effective to sterilize said biological material at a rate effective to sterilize and protect said biological material from said radiation,
wherein said residual solvent content of said biological material is reduced to a level effective to preserve said biological material and said biological material is glassy or vitrified.

46. The method of claim 45, wherein said residual solvent content is less than 5%.

47. The method of claim 45, wherein said residual solvent content is less than 2%.

48. The method of claim 45, wherein said residual solvent content is less than 1%.

49. The method of claim 45, wherein said residual solvent content is less than 0.5%.

50. The method of claim 45, wherein said residual solvent content is less than 0.08%.

51. The method of claim 37 or 45, wherein said biological material is selected from the group consisting of monoclonal immunoglobulins, polyclonal immunoglobulins, glycosidases, sulfatases, urokinase and Factor VIII.

52. The method according to claim 37 or 45, wherein said biological material is selected from the group consisting of cells, tissues, blood, blood components, proteins, enzymes, immunoglobulins, botanicals, food, ligaments, tendons, nerves, bone, demineralized bone matrix, grafts, joints, femurs, femoral heads, teeth, skin grafts, bone marrow, heart valves, cartilage, corneas, arteries, veins, meat, organs, limbs, digits, lipids, carbohydrates, collagen, chitin, stem cells, islet of Langerhans cells, genetically altered cells, red blood cells, white blood cells, proteinaceous material and combinations thereof.

53. The method according to claim 52, wherein said blood components are selected from the group consisting of cellular blood components, blood proteins, liquid blood components and combinations thereof.

54. The method according to claim 52, wherein said collagen is selected from the group consisting of native collagen, afibrillar collagen, atelomeric collagen, soluble collagen and insoluble collagen.

55. The method according to claim 52, wherein said biological material comprises a protein or peptide produced from cell culture.

56. The method according to claim 37 or 45, wherein said biological material is whole or processed.

57. The method according to claim 37 or 45, wherein said biological material is selected from the group consisting of hearts, livers, lungs, kidneys, intestines and pancreas.

58. The method according to claim 37 or 45, wherein said biological material is human.

59. The method according to claim 37 or 45, wherein said biological material is mammalian.

60. The method according to claim 37 or 45, wherein said biological material is bovine.

61. The method according to claim 37 or 45, wherein said biological material is equine.

62. The method according to claim 37 or 45, wherein said biological material is porcine.

63. The method according to claim 37 or 45, wherein said biological material is transgenic or recombinant.

64. The method according to claim 63, wherein said biological material is milk.

65. The method according to claim 37 or 45, wherein said biological material is milk, collagen, plasma or serum.

66. The method according to claim 37 or 45, wherein said biological material is selected from the group consisting of ligaments, tendons, nerves, bone, teeth, bone marrow, skin grafts, cartilage, corneas, arteries, veins and organs for transplantation.

67. The method according to claim 37 or 45, wherein said biological material is tissue.

68. The method according to claim 67, wherein said tissue is selected from the group consisting of bone, grafts, joints, femurs, femoral heads, heart valves, ligaments, hearts, livers, lungs, kidneys, intestines, pancreas, limbs, digits and demineralized bone matrix.

69. The method according to claim 37 or 45, wherein said biological material is bovine serum.

70. The method according to claim 69, wherein said biological material is fetal bovine serum.

* * * * *